US009057088B2

(12) United States Patent
Freeman et al.

(10) Patent No.: US 9,057,088 B2
(45) Date of Patent: Jun. 16, 2015

(54) BIOLOGICALLY ACTIVE SILVER-COATED PROTEINS

(75) Inventors: Amihay Freeman, Ben-Shemen (IL); Yosi Shacham-Diamand, Zikhron-Yaakov (IL); Hila Moscovich-Dagan, Hod-HaSharon (IL); Noa Hadar, Hod-HaSharon (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 1627 days.

(21) Appl. No.: 11/795,924

(22) PCT Filed: Jan. 26, 2006

(86) PCT No.: PCT/IL2006/000115
§ 371 (c)(1),
(2), (4) Date: Jul. 24, 2007

(87) PCT Pub. No.: WO2006/080017
PCT Pub. Date: Aug. 3, 2006

(65) Prior Publication Data
US 2009/0291070 A1   Nov. 26, 2009

Related U.S. Application Data

(60) Provisional application No. 60/671,073, filed on Apr. 14, 2005, provisional application No. 60/646,648, filed on Jan. 26, 2005.

(51) Int. Cl.
| *A61K 38/44* | (2006.01) |
| *A61K 38/16* | (2006.01) |
| *C12Q 1/00* | (2006.01) |
| *C07K 14/00* | (2006.01) |

(52) U.S. Cl.
CPC .............. *C12Q 1/006* (2013.01); *C07K 14/00* (2013.01); *C12Q 1/001* (2013.01)

(58) Field of Classification Search
None
See application file for complete search history.

(56) References Cited

U.S. PATENT DOCUMENTS

| 4,554,254 | A | * | 11/1985 | Krystal ............................ 436/86 |
| 4,679,562 | A | | 7/1987 | Luksha et al. |
| 6,042,848 | A | | 3/2000 | Lawyer et al. |
| 2003/0175207 | A1 | | 9/2003 | Olstein et al. |
| 2004/0063915 | A1 | * | 4/2004 | Diner et al. ................ 530/391.1 |
| 2004/0074785 | A1 | | 4/2004 | Holker et al. |
| 2004/0082766 | A1 | | 4/2004 | Hanzawa et al. |
| 2009/0127112 | A1 | | 5/2009 | Freeman et al. |

FOREIGN PATENT DOCUMENTS

| EP | 0173629 | 3/1986 |
| EP | 235024 | 9/1987 |
| EP | 0235024 | 9/1987 |
| EP | 0359428 | 3/1990 |
| GB | 2171104 | 8/1986 |
| WO | WO 86/01410 | 3/1986 |
| WO | WO 93/15117 | 8/1993 |
| WO | WO 01/27628 | 4/2001 |
| WO | WO 2004/073640 | 9/2004 |
| WO | WO 2006/080017 | 8/2006 |
| WO | WO 2006/123343 | 11/2006 |

OTHER PUBLICATIONS

Naik R.R. et al. Biomimetic synthesis and patterning of silver nanoparticles, Nature Materials, Nov. 2002, vol. 1 , pp. 169-172 (Published Online: Oct. 27, 2002).*
Kumar R. et al. Hepatic silver binding protein (Ag BP) from sparrow (*Passer domesticus*), Experientia, 1979, vol. 35, pp. 1621-1623.*
Copeland R. A. et al. Surface-enhanced Raman spectra of an active flavo enzyme: Glucose oxidase and riboflavin binding proteins on silver particles, J. Am. Chem. Soc., 1984, vol. 106, pp. 3872-3874.*
Vidugiris G. et al. Complex formation of amino acids and proteins with silver ions, Bioelectrochemistry and Bioenergetics, 1988, vol. 19, pp. 513-520.*
Frederick K. R. et al., Glucose oxidase from *Aspergillus niger*: Cloning, gene sequencing, secretion from *Saccharomyces cerevisiae* and kinetic analysis of a yeast-derived enzyme, The Journal of Biological Sciences, 1990, vol. 265, No. 7, pp. 3793-3802.*
U2—Creighton J. A. et al. Plasma Resonance Enhancement of Raman Scattering by Pyridine Adsorbed on Silver or Gold Sol Particles of Size Comparable to the Excitation Wavelength, J. Am. Chem. Soc., Faraday Trans. 2, 1979, vol. 75, pp. 790-798.*
Dion A.S. et al. Ammonical silver staining of proteins: Mechanism of glutaraldehyde enhancement, Analytical Biochemistry, 1983, vol. 129, pp. 490-496.*
Rembaum A. et al. Polyglutaraldehyde: A new reagent for coupling proteins to microspheres and for labeling cell-surface receptors, Journal of Immunological Methods, 1978, vol. 24, pp. 239-250.*
Basu A. et al., Preparation of Enzyme Conjugate through Adipic Acid Dihydrazide as Linker and Its Use in Immunoassays, Clinical Chemistry, 2003, vol. 49, No. 8, pp. 1410-1412.*
Communication Relating to the Results of the Partial International Search Dated Dec. 27, 2006 From the International Searching Authority Re.: Application No. PCT/IL2006/000587.

(Continued)

*Primary Examiner* — Satyendra Singh

(57) ABSTRACT

Silver-coated proteins, being dissolvable or suspendable in aqueous media and/or retaining a biological activity of the protein and a process for preparing same are disclosed. Further disclosed are modified proteins which have a reducing moiety attached to the surface thereof and a process for preparing same. The modified proteins can be utilized for obtaining the silver-coated proteins. Further disclosed are a pharmaceutical composition containing and a method of treating bacterial and fungal infections utilizing biologically active silver-coated hydrogen peroxide producing enzymes such as glucose oxidase. Further disclosed are conductive elements that comprise the silver-coated proteins disclosed herein and electronic circuits containing same. Further disclosed are electrodes having the silver-coated proteins deposited thereon and biosensor systems utilizing same for determining a level of an analyte in a liquid sample.

18 Claims, 6 Drawing Sheets
(5 of 6 Drawing Sheet(s) Filed in Color)

(56) References Cited

OTHER PUBLICATIONS

International Preliminary Report on Patentability Dated Aug. 9, 2007 From the International Bureau of WIPO Re.: Application No. PCT/IL2006/000115.
International Preliminary Report on Patentability Dated Nov. 29, 2007 From the International Bureau of WIPO Re.: Application No. PCT/IL2006/000587.
Communication Pursuant to Article 94(3) EPC Dated May 23, 2008 From the European Patent Office Re.: Application No. 06701722.8.
Communication Relating to the Results of the Partial International Search Dated Jan. 26, 2006 From the International Searching Authority Re.: Application No. PCT/IL2006/000115.
International Search Report Dated Jul. 5, 2006 From the International Searching Authority Re.: Application No. PCT/IL2006/000115.
International Search Report Dated May 11, 2007 From the International Searching Authority Re.: Application No. PCT/IL2006/000587.
Written Opinion Dated Jul. 5, 2006 From the International Searching Authority Re.: Application No. PCT/IL2006/000115.
Written Opinion Dated May 11, 2007 From the International Searching Authority Re.: Application No. PCT/IL2006/000587.
Becker "Silver Ions in the Treatment of Local Infections", Metal-Based Drugs, 6(4-5): 311-314, 1999. p. 311.
Das et al. "Integration of Photosynthetic Protein Molecular Complexes in Solid-State Electronic Devices", Nano Letters, 4(6): 1079-1083, 2004.
Ferapontova et al. "Effect of Cysteine Mutations on Direct Electron Transfer of Horseradish Peroxidase on Gold", Biosensors and Bioelectronics, 17(11-12): 953-963, 2002. Abstract, Figs.2, 3.
Ferretti et al. "Self-Assembled Monolayers: A Versatile Tool for the Formulation of Bio-Surfaces", Trends in Analytical Chemistry, 19(9): 530-540, 2000.
Frolov et al. "Fabrication of a Photoelectronic Device by Direct Chemical Binding of the Photosynthetic Reaction Center Protein to Metal Surfaces", Advanced Materials, 17: 2434-2437, 2005.
Invitation Pursuant to Article 94(3) and Rule 71(1) EPC Dated Feb. 18, 2010 From the European Patent Office Re.: Application No. 06701722.8.
Response Dated Apr. 11, 2010 to Invitation Pursuant to Article 94(3) and Rule 71(1) EPC of Feb. 18, 2010 From the European Patent Office Re.: Application No. 06701722.8.
Official Action Dated Apr. 14, 2010 From the US Patent and Trademark Office Re.: U.S. Appl. No. 11/920,689.
Response Dated May 13, 2010 to Official Action of Apr. 14, 2010 From the US Patent and Trademark Office Re.: U.S. Appl. No. 11/920,689.
Official Action Dated Nov. 23, 2010 From the US Patent and Trademark Office Re.: U.S. Appl. No. 11/920,689.
Habicht et al. "Characterization of metal Decorated Protein Templates by Scanning Electron/Scanning Force Microscopy and Microanalysis", Surface and Interface Analysis, 36: 720-723, 2004.
Knez et al. "Spatially Selective Nucleation of metal Clusters on the Tobacco Mosaic Virus", Advanced Functional Materials, 14(2): 116-124, Feb. 2004.
Scheibel et al. "Conducting Nanowires Built by Controlled Self-Assembly of Amyloid Fibers and Selective Metal Deposition", Proc. Natl. Acad. Sci. USA, PNAS, 100(8): 4527-4532, Apr. 15, 2003.
Official Action Dated Jul. 28, 2010 From the US Patent and Trademark Office Re.: U.S. Appl. No. 11/920,689.
Dujardin et al. "Organization of Metallic Nanoparticles Using Tobacco Mosaic Virus Templates", Nano Letters, 3(3): 413-417, 2003.
Response Dated Aug. 30, 2010 to Official Action of Jul. 28, 2010 From the US Patent and Trademark Office Re.: U.S. Appl. No. 11/920,689.
Dagan-Moscovich et al. "'Nano Wiring' of the Catalytic Site of Novel Molecular Enzyme-Metal Hybrids to Electrodes", Journal of Physical Chemistry C, 2007, Manuscript, pp. 1-15.
Communication Pursuant to Article 94(3) EPC Dated Aug. 24, 2009 From the European Patent Office Re.: Application No. 06701722.8.
Becker "Silver Ions in the Treatment of Local Infections", Metal-Based Drugs, XP008063656, 6(4-5): 311-314, 1999. p. 311.
Ferapontova et al. "Effect of Cysteine Mutations on Direct Electron Transfer of Horseradish Peroxidase on Gold", XP002379013, Biosensors and Bioelectronics, 17(11-12): 953-963, 2002. Abstract, Figs.2, 3.
Ben-Yoav et al. "Enzymatically Attenuated In Situ Release of Silver Ions to Combat Bacterial Biofilms: A Feasibility Study", Journal of Drug Delivery Science and Technology, 18(1): 25-29, 2009.
Response Dated Feb. 23, 2011 to Official Action of Nov. 23, 2010 From the US Patent and Trademark Office Re.: U.S. Appl. No. 11/920,689.
Official Action Dated Apr. 26, 2011 From the US Patent and Trademark Office Re.: U.S. Appl. No. 11/920,689.
Free Online Dictionary "Elemental", Definition of the Term, The Free Online Dictionary, Thesaurus and Encyclopedia, p. 1, Apr. 18, 2011.
Official Action Dated May 19, 2014 From the US Patent and Trademark Office Re. U.S. Appl. No. 11/920,689.
Beveridge et al. "Sites of Metal Deposition in the Cell Wall of *Bacillus subtilis*", Journal of Bacteriology, 141(2): 876-887, Feb. 1980.
Official Action Dated Nov. 10, 2014 From the US Patent and Trademark Office Re. U.S. Appl. No. 11/920,689.

\* cited by examiner

BIOLOGICALLY ACTIVE SILVER-COATED PROTEINS

RELATED APPLICATIONS

This Application is a National Phase of PCT Patent Application No. PCT/IL2006/000115 having International Filing Date of Jan. 26, 2006, which claims the benefit of U.S. Provisional Patent Application Nos. 60/671,073 filed on Apr. 14, 2005 and 60/646,648 filed on Jan. 26, 2005. The contents of the above Applications are all incorporated herein by reference.

FIELD AND BACKGROUND OF THE INVENTION

The present invention relates to novel biologically active composites and uses thereof and, more particularly, to biologically active silver-coated proteins, to integration thereof in biosensors and electronic devices and to pharmaceutical compositions containing and methods of treatment utilizing same. The present invention further relates to processes and intermediates for the preparation of such composites.

Electroless deposition is a widely known technique for depositing metals such as, for example, copper, silver and cobalt, on various surfaces. In principle, electroless deposition is performed in electrolytic solutions or fluids (e.g., aqueous solutions of metal ions) without applying an external voltage, and is effected by an electrochemical reaction between the metal ions and a reducing agent. The electrolytic solution may optionally further include complexing agents and pH adjusting agents and the process can optionally be performed on a catalytic surface (e.g., of a semiconductor wafer).

Electroless deposition is presently known as a highly suitable technique for forming metal films and coatings on microscopic elements and areas on substrates surfaces, for forming barriers and interconnects between different layers on semiconducting wafers and for creating microscopic reservoirs of metallic atoms at specific sites of a subject carrier element.

Hence, at present, electroless deposition is mostly utilized in the manufacture of devices on semiconductor wafers, and particularly in the fabrication of multiple levels of conductive layers, typically of metals such as copper, on a substrate surface.

Electroless deposition is further presently utilized in several biological and medical applications. One example for such an application is the treatment and prevention of tooth cavities, which is effected by depositing a thin metal film onto tooth enamel. The deposited metal films exhibited high adherence to the tooth and maintained the bulk metal properties.

Biosensors such as those disclosed, for example, in U.S. Pat. Nos. 6,773,564, 6,776,888, 6,982,027, 6,984,307, 6,942,770 and Japanese Patent No. 2517153, are analytical devices which convert a biological response into an electrical signal, and thus can quantitatively and qualitatively determine a specific biochemical analyte in a sample. Biosensors can be produced by forming an electrode system having a working electrode (also referred to as "measuring electrode") and a counter electrode on an electrically insulating substrate, and then forming a reactive layer including, for example, a redox enzyme that reacts with the biochemical analyte. When the reactive layer is in contact with a sample containing the analyte, the analyte is catalytically oxidized by the redox enzyme. The catalytic reaction is typically performed in the presence of an electron-transfer mediator, which is reduced upon the oxidation reaction and is then re-oxidized electrochemically. The concentration of the analyte in the sample is determined upon the recorded oxidation current values.

Another example is the manufacturing of enzyme-containing nanoelectrodes for ultra-sensitive amperometric detection of glucose at low overpotentials. Thus, for example, gold nanotubular electrode ensembles were prepared by electroless depositing the metal within the pores of polycarbonate track-etched membranes. Mono-enzyme glucose oxidase and monolayer/bilayer bi-enzyme glucose oxidase/horseradish peroxidase bioelectrodes were prepared by immobilizing the enzymes onto gold nanotubes surfaces modified with mercaptoethylamine. An advantageous feature of the bi-enzyme electrodes is the possibility to detect glucose at very low applied potentials where the noise level and interferences from other electro-oxidizable compounds are minimal.

Glucose oxidase-containing biosensors for detecting glucose involve a catalytic conversion of glucose to gluconic acid by the enzyme glucose oxidase. This catalytic reaction is coupled to oxygen, and leads to the production of hydrogen peroxide under physiological conditions.

However, electrochemical biosensors based on hydrogen peroxide detection often suffer from substantial inaccuracies, resulting from fluctuations in local oxygen concentrations and the stoichiometric limitation of glucose, known in the field as "oxygen deficit". This adverse phenomenon may be overcome by introducing synthetic mediators that can react rapidly with the enzyme in its reduced form, and minimize competition with oxygen. Ferrocene (Fc) and derivatives thereof are among the most widely used mediators for that purpose [Dong, S. J. et al., *Biosensors & Bioelectronics*, 1992, 7, 215-222]. However, the use of Fc and its derivatives as mediators is limited by poor absorption on the electrode surface. Fc and its derivatives are highly soluble in aqueous solutions, especially when in an oxidized/charged form (Fc+), and therefore diffuse away from the immobilized enzyme located on the electrode surface, rendering the whole process inefficient.

Other examples include metallization of various biological moieties by electroless deposition. Thus, electroless deposition of natural arrays of proteins was recently successfully demonstrated for the fabrication of nanowires from microtubules, viral envelopes, amyloid fibers and actin filaments.

The protein metallization described above was effected by techniques that involve nucleation and enlargement by electroless plating. Nucleation was typically performed by adsorption of palladium or platinum ions onto the surface of the biological moiety, followed by chemical reduction thereof, or, alternatively, by surface labeling with colloidal gold particles. Enlargement of the nucleation sites thus obtained into continuously deposited metallic films was typically carried out by immersion in a plating solution containing the metal ions of choice (e.g., $Ag^{+1}$ or $Ni^{+2}$) and reducing agents (e.g., $NaBH_4$ or dimethylaminoborane). These techniques typically result in the formation of a relatively thick metal deposition, of e.g., 10 to 35 nanometers. These techniques further lead to the loss of the proteins native biological activity due to deformation and denaturation, blockage of active and binding sites, and gross precipitation of the protein, which most likely results from the strong and incontrollable reducing aptitude of the reducing agent used.

Thus, while the presently known methods for metallizing biological moieties by electroless deposition involve proteins that are either immobilized and/or inactivated before, during and/or as a result of the deposition process, the ability and utility to deposit metals onto a single, soluble biological moiety, particularly protein, while maintaining its activity, dissolvability and other parameters was not demonstrated hitherto. Such a metallization should be performed while maintaining features such as the native chemical structure, the motility and thus the biological activity of the protein. The presently known electroless deposition methods, however, typically interfere with these features and hence do not allow the provision of metallized yet active proteins.

The metallization of proteins while maintaining their activity and/or dissolvability is highly advantageous since it may potentially provide novel therapeutically active agents which may exert, for example, multiples activities resulting from the biologically active protein and/or an active metal coating, and may further be utilized as novel molecular tools for applications such as wiring of nano-sized sensors to composite biochips [I. Wilner and E. Katz. *Angew. Chem. Int. Ed.* 2000, 39, pp. 1180-1218].

European Patent No. EP00173629B1 teaches the attachment of metal-ion chelating moieties to surface glycans of antibodies, to thereby form conjugates of antibodies and chelating moieties while maintaining the immunoreactivity and immunospecificity of the antibodies. The attachment of the chelating moieties, according to this patent, is effected by generation of aldehyde groups on the surface glycans of the antibody, followed by the conjugation thereto of chelating moieties that have a free amine group, so as to form, under mild conditions, a Schiff-base between the aldehyde group on the antibody's surface and the amine group of the chelating moiety. The resulting conjugate is then used for complexing metal ions via the chelating moieties. This patent, however, fails to teach or suggest the conjugation of reducing moieties that may participate in the more active reduction process involved in electroless deposition, to proteins, while maintaining the activity or dissolvability of proteins, and particularly proteins other than antibodies.

SUMMARY OF THE INVENTION

The prior art fails to teach methods of electroless deposition of metals on proteins surface, while maintaining the activity and/or dissolvability of proteins. As discussed hereinabove, metallized proteins which are active and/or dissolvable can be beneficially utilized as therapeutically active agents which may exert, for example, multiples activities resulting from the biologically active protein and/or an active metal coating, and may further be utilized as novel molecular tools for applications such as wiring of nano-sized sensors to composite biochips.

There is thus a widely recognized need for, and it would be highly advantageous to have a novel method for depositing metals, particularly silver, on the surface of proteins, which would allow the preparation of metal-coated yet dissolvable and active proteins.

While conceiving the present invention, it was envisioned that such metal-coated yet dissolvable and active proteins can be obtained by site-specifically modifying certain surface groups on the protein surface and attaching thereto reducing moieties that can participate in the electroless deposition of the metal (e.g., silver) on the protein's surface, whereby both the modification of the surface groups and the reduction process involved are performed under conditions that do not affect neither the biological activity nor the dissolvability of the protein.

While reducing the present invention to practice, the present inventors have developed and successfully practiced a novel methodology for preparing silver-coated proteins, particularly enzymes, by modifying surface groups of the protein and attaching thereto reducing moieties which effectively, and yet mildly, may participate in an in situ electroless deposition of metallic silver particles on the protein surface. Using this methodology, the present inventors have prepared various biologically active and/or dissolvable silver-coated proteins, which were found highly effective in, for example, the treatment of bacterial and fungal infections and in the construction of electrochemical biosensors.

Thus, according to one aspect of the present invention there is provided a composition-of-matter which comprises a protein having a surface and a silver coating deposited over at least a portion of the surface and forming a silver-coated protein that is dissolvable or suspendable in an aqueous medium.

According to further features in preferred embodiments of the invention described below, the protein has a biological activity and the silver-coated protein retains the biological activity.

According to another aspect of the present invention there is provided a composition-of-matter which comprises a protein having a surface and further having a biological activity and a silver coating deposited over at least a portion of the protein surface which forms a silver-coated protein retaining its original biological activity.

According to features in preferred embodiments of the above aspect, the silver-coated protein is dissolvable or suspendable in an aqueous medium.

According to still further features in the described preferred embodiments the surface of each of the proteins described above includes an oxidized reducing moiety attached to at least a portion thereof.

According to further features in preferred embodiments of the invention described below, the silver-coated protein comprises a protein which is selected from the group consisting of an antibody, a lectin, a nucleic acid binding protein, a cellular protein, a serum protein, a growth factor, a hormone, an enzyme, a glycoprotein and a transcription factor, and is preferably an enzyme.

According to yet another aspect of the present invention there is provided a composition-of-matter which comprises a protein having one or more reducing moieties conjugated thereto, whereby the reducing moieties are selected so as to allow retaining the biological activity of the protein. The protein according to this aspect of the present invention can be any protein, as described hereinabove, excluding an antibody.

According to further features in preferred embodiments of the invention described below, the protein having one or more reducing moieties conjugated thereto is dissolvable or suspendable in an aqueous medium.

According to still further features in the described preferred embodiments the reducing moieties are capable of converting silver ions into metallic silver.

According to still further features in the described preferred embodiments the protein is an enzyme such as, for example, glucose oxidase and horseradish peroxidase.

According to still further features in the described preferred embodiments the enzyme is a hydrogen peroxide producing enzyme.

According to still further features in the described preferred embodiments the silver-coated protein is prepared by contacting a modified protein with an aqueous solution of silver ions, whereby the modified protein comprises a protein having a surface and one or more reducing moieties being conjugated to the surface.

Thus, according to yet another aspect of the present invention there is provided a process of preparing a protein having one or more reducing moieties conjugated thereto, whereby the reducing moieties are selected so as to allow retaining a biological activity of the protein. The process according to this aspect of the present invention comprises: providing a protein having one or more reactive groups on its surface; and conjugating to one or more of the reactive groups one or more chemical moieties selected such that upon the conjugation a protein having one or more reducing moieties attached to its surface is obtained.

According to further features in preferred embodiments of the invention described below, the protein has a biological activity and the modified protein having the reducing moieties attached to its surface retains the biological activity.

According to an additional aspect of the present invention there is provided a process of preparing a silver-coated protein such as the silver-coated protein described herein. The process according to this aspect of the present invention comprises: providing a first aqueous solution containing silver ions; providing a protein having a first reactive group on a surface thereof; conjugating to the first reactive group a first chemical moiety selected such that upon the conjugating a protein having a first reducing moiety attached to its surface is obtained; and contacting the protein having the first reducing moiety attached to its surface with the first aqueous solution containing silver ions, to thereby form a first silver coating on at least a first portion of the surface of the protein.

According to further features in preferred embodiments of the invention described below, the process of preparing a silver-coated protein further comprises: providing a second aqueous solution containing silver ions; providing a silver-coated protein having a second reactive group on a surface thereof, which has a first silver coating deposited on at least a portion of its surface; conjugating to the second reactive group a second chemical moiety selected such that upon the conjugating a protein having a second reducing moiety attached to its surface is obtained; and contacting the protein having the second reducing moiety attached to its surface with the second aqueous solution containing silver ions, to thereby form a second silver coating on at least a second portion of the surface of the protein.

According to further features in preferred embodiments of the invention described below, the conjugation is effected between the reactive group and a first functional group that forms a part of the chemical moiety.

According to still further features in the described preferred embodiments, the reducing moiety is formed upon conjugating the first functional group and the reactive group.

According to still further features in the described preferred embodiments, the reducing moiety is a second functional group that forms a part of the chemical moiety.

According to still further features in the described preferred embodiments, providing the protein having one or more reactive groups on its surface comprises: providing a protein having one or more functional moieties on a surface thereof, which include a third functional group; and converting the third functional group into the reactive group.

According to a further aspect of the present invention there is provided a pharmaceutical composition that is identified for use in the treatment of a bacterial and/or fungal infection, which comprises, as an active ingredient, a silver-coated hydrogen peroxide producing enzyme, and a pharmaceutically acceptable carrier.

According to further features in the preferred embodiments of the invention, the pharmaceutical composition is being packaged in a packaging material and identified in print, in or on said packaging material, for use in the treatment of the abovementioned infection.

According to still an additional aspect of the present invention there is provided a method of treating a bacterial and/or fungal infection, which comprises administering to a subject in need thereof a therapeutically effective amount of silver-coated hydrogen peroxide producing enzyme.

According to further features in the described preferred embodiments, a substrate of the hydrogen peroxide producing enzyme is a sugar, and preferably the sugar is glucose. Still preferably the enzyme is glucose oxidase According to yet a further aspect of the present invention there is provided a conductive element comprising silver-coated protein.

According to further features in the described preferred embodiments of the invention, the conductive element has a size that ranges between 1 and 1000 nanometer.

According to still a further aspect of the present invention there is provided an electronic circuit assembly which includes an arrangement of conductive elements interconnecting a more than one electronic elements wherein at least some of the conductive elements include a silver-coated protein.

According to another aspect of the present invention there is provided an electrode which comprises the composition-of-matter presented herein deposited thereon.

According to still a further aspect of the present invention there is provided a biosensor system for electrochemically determining a level of an analyte in a liquid sample, the system comprising an insulating base; and an electrode system which includes the electrode described herein, wherein the protein in the composition-of-matter is selected capable of chemically reacting with the analyte while producing a transfer of electrons.

According to further features in preferred embodiments of the invention described below, the system further comprises a counter electrode.

According to further features in the described preferred embodiments, the system further comprises an electron transfer mediator.

According to yet a further aspect of the present invention there is provided a method of electrochemically determining a level of an analyte in a liquid sample, which comprises contacting the biosensor system described herein with the liquid sample and measuring the transfer of electrons, thereby determining the level of the analyte in the sample.

According to further features in preferred embodiments of the invention described below, the protein is an oxidoreductase enzyme.

According to still further features in the preferred embodiments, the enzyme is a hydrogen peroxide producing enzyme such as glucose oxidase.

According to still further features in the preferred embodiments, the biosensor system and method are used for determining a level of glucose in a liquid sample.

The present invention successfully addresses the shortcomings of the presently known configurations by providing silver-coated proteins, which substantially retain the biological activity and/or dissolvability of the uncoated protein, and can therefore be utilized in various therapeutic applications and in forming biosensors and electronic circuitry assemblies.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

As used herein, the singular form "a", "an" and "the" include plural references unless the context clearly dictates otherwise. For example, the term "a protein" or "at least one protein" may include a plurality of proteins, including mixtures thereof.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein throughout, the term "comprising" means that other steps and ingredients that do not affect the final result can be added. This term encompasses the terms "consisting of" and "consisting essentially of".

As used herein, the phrase "substantially retaining" and/or "substantially maintaining" refers to a protein's specific activity, dissolvability and other biochemical properties essential to its biological activity, which are retained and or maintained at significant levels subsequent to the chemical modifications, described in the present invention, carried out so to obtain a metal-coat on the protein and intermediates to that end.

The term "method" or "process" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

BRIEF DESCRIPTION OF THE DRAWINGS

The file of this patent contains at least one drawing executed in color photograph. Copies of this patent with color photograph(s) will be provided by the Patent and Trademark Office upon request and payment of necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

Figure 1:
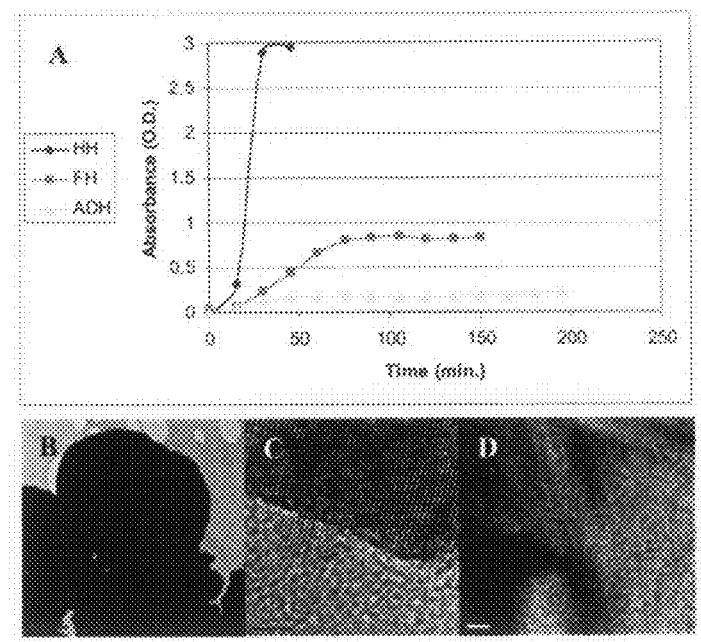
Figure 2:
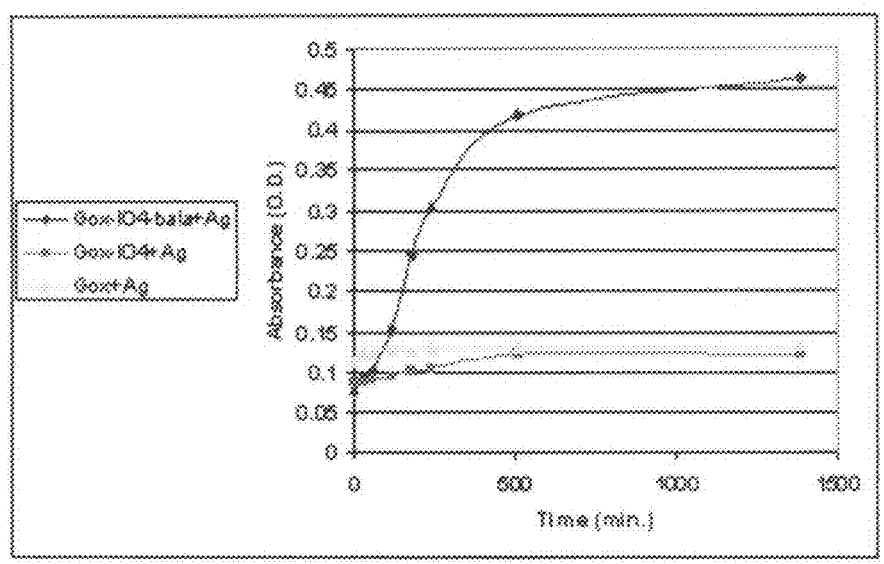
Figure 3:
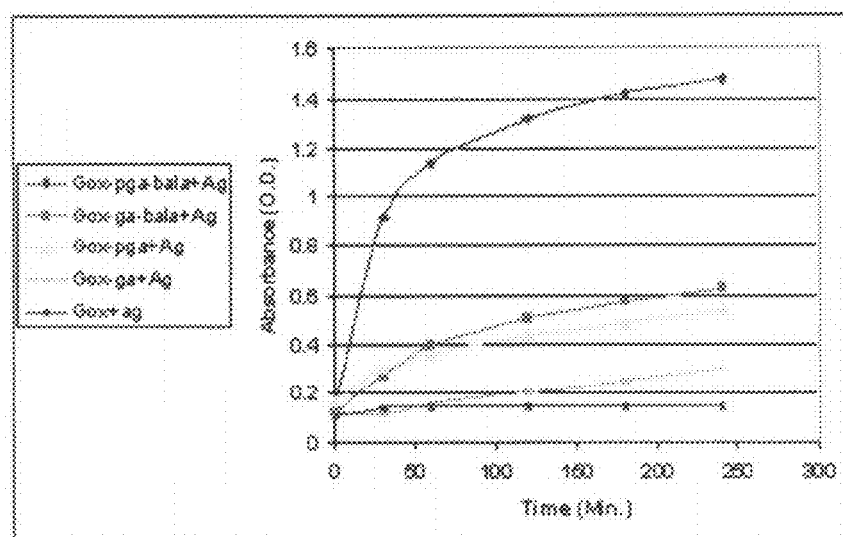
Figure 4:
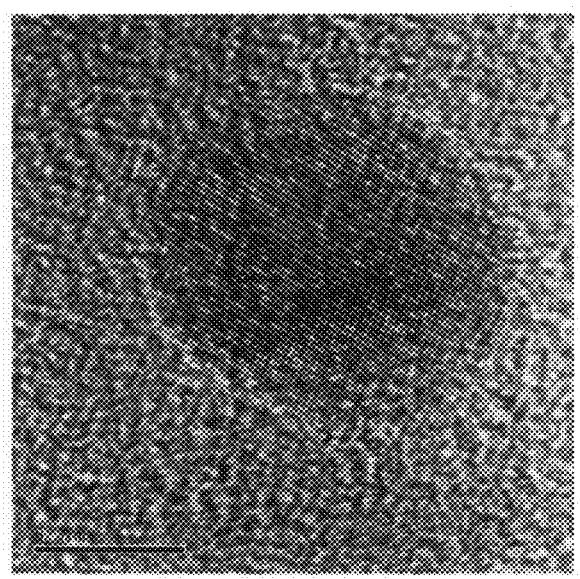
Figure 5:
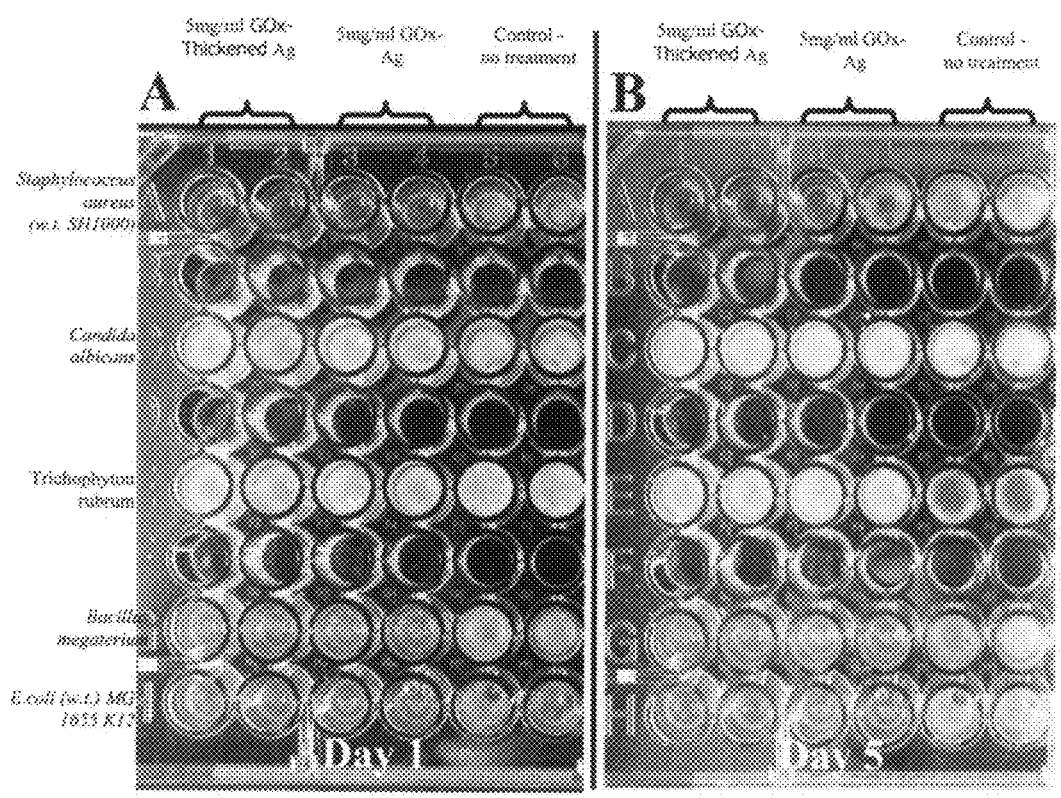
Figure 6:
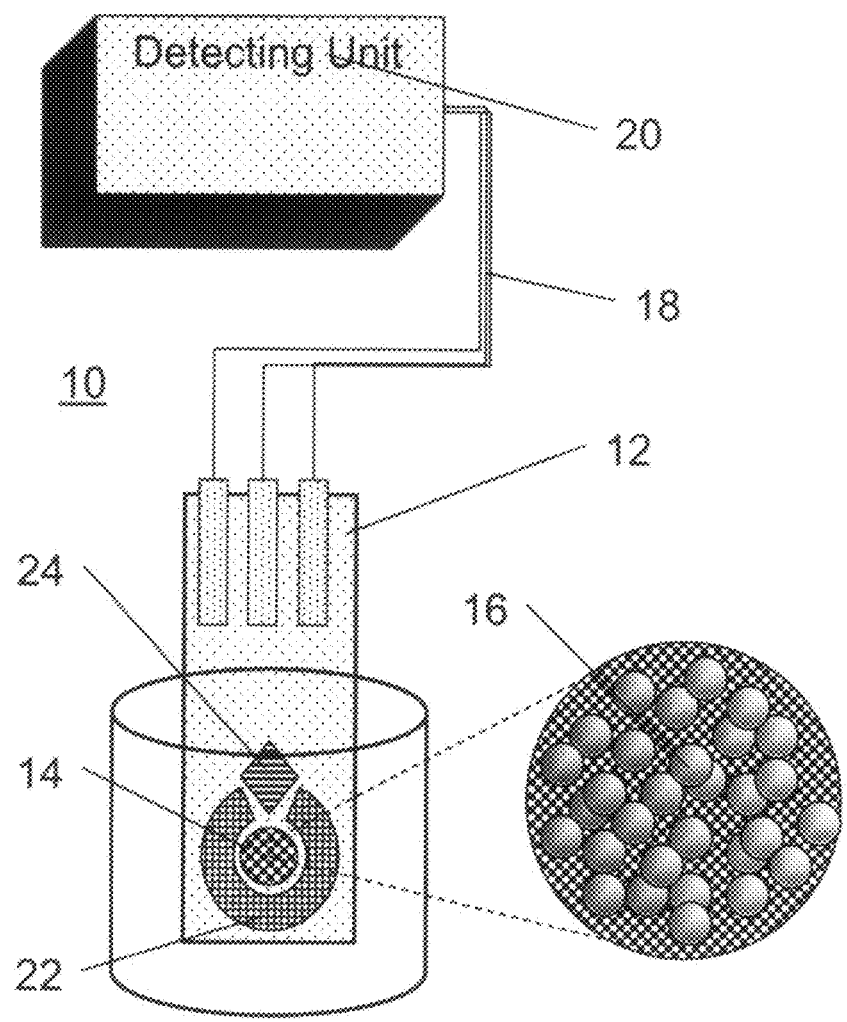
Figure 7:
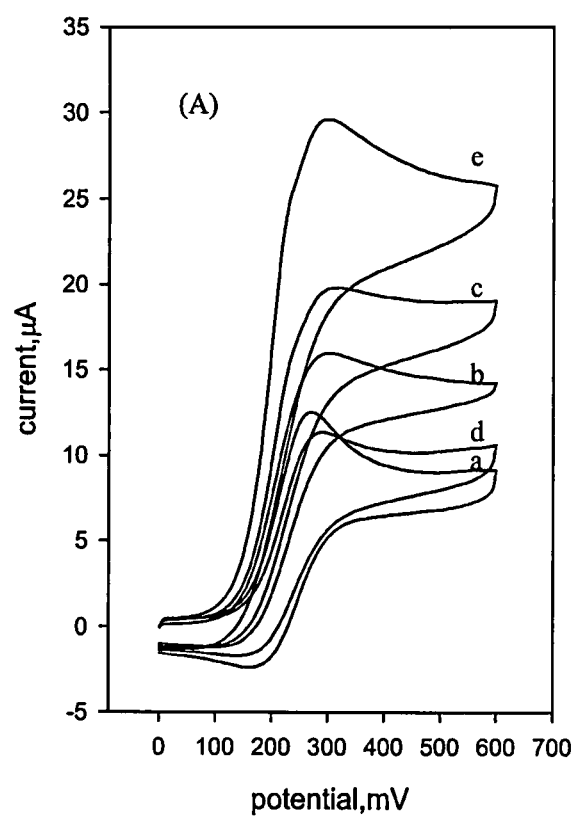
Figure 8:
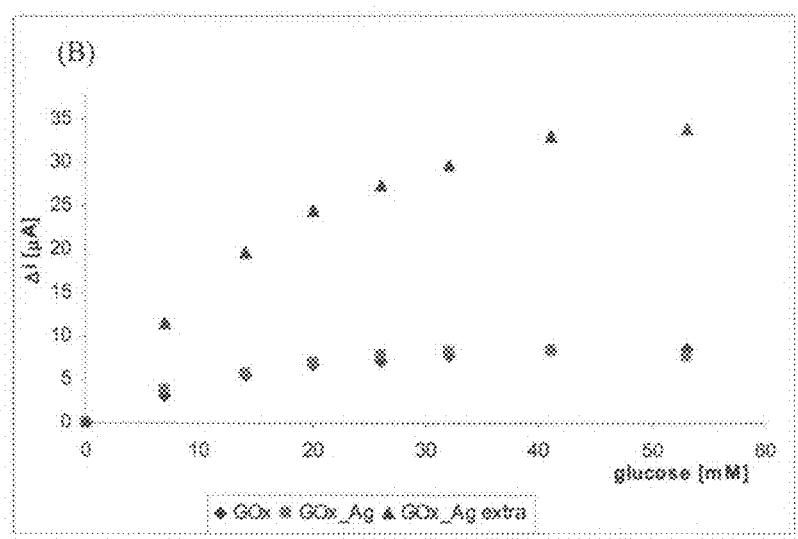

FIGS. 1($a$-$d$) present a comparative plot showing the reduction rate of silver nitrate in solution, monitored spectrophotometrically at 450 nm, using hydrazine (HH, diamonds), formic hydrazide (FH, squares) and adipic dihydrazide (ADH, triangles) as reducing agents (FIG. 1$a$), and high resolution electron micrographs, obtained without staining, of silver particles obtained by reducing silver ions by hydrazine (FIG. 1$b$, scale bar of 2 μm), formic hydrazide (FIG. 1$c$, scale bar of 5 nm), and adipic dihydrazide (FIG. 1$d$, scale bar of 2 nm);

FIG. 2 presents comparative plots showing the reduction rate of silver nitrate on the surface of glucose oxidase, monitored spectrophotometrically at 398 nm, for the native enzyme (Gox+Ag, triangles), periodate-treated enzyme (Gox-IO$_4^-$+Ag, squares), periodate-treated and β-alanine-treated enzyme (Gox-IO$_4^-$-bala+Ag, diamonds);

FIG. 3 presents a comparative plot showing the reduction rate of silver nitrate on the surface of glucose oxidase, monitored spectrophotometrically at 450 nm, for the native enzyme (Gox+Ag, stars), glutaraldehyde-treated enzyme (Gox-ga+Ag, crosses), polyglutaraldehyde-treated enzyme (Gox-pga+Ag, triangles), glutaraldehyde-treated and β-alanine-treated enzyme (Gox-ga-bala+Ag, squares), and polyglutaraldehyde-treated and β-alanine-treated glucose oxidase (Gox-pga-bala+Ag, diamonds);

FIG. 4 presents a high resolution electron micrograph, obtained without further staining of the sample, of a layer of silver atoms deposited on glucose oxidase by activation of the enzyme surface with periodate and conjugation to β-alanine so as to form a Schiff-base type reducing moiety, showing a patch of about 11 nm in diameter of crystalline silver on the surface of the enzyme (scale bar of 5 nm);

FIGS. 5($a$-$b$) present images of an ELISA plate in which various microorganism samples were grown and introduced to untreated glucose oxidase (control), silver-coated glucose oxidase and to a thickened silver-coated glucose oxidase (doubly silver-coated), one day (FIG. 5$a$) and 5 days (FIG. 5$b$) after introduction of the enzyme;

FIG. 6 presents a schematic illustration of a biosensor system which comprises an electrode having a silver-coated protein deposited thereon, according to embodiments of the present invention;

FIG. 7 presents comparative cyclic voltammograms of electro-catalytic currents (in microamperes) plotted versus electric potential (in millivolts) recorded for a glucose biosensor micro-electrode having deposited thereon (a) untreated glucose oxidase, (b) polyglutaraldehyde-treated glucose oxidase, (c) polyglutaraldehyde and β-alanine-treated glucose oxidase, (d) polyglutaraldehyde and β-alanine-treated glucose oxidase coated with silver and (e) polyglutaraldehyde and β-alanine-treated glucose oxidase doubly coated with silver; and FIG. 8 presents comparative plots showing the electro-catalytic peak currents plotted versus glucose concentration as recorded for a glucose biosensor micro-electrode having deposited thereon untreated glucose oxidase (blue diamonds), polyglutaraldehyde and β-alanine-treated glucose oxidase coated with silver (magenta rectangles) and polyglutaraldehyde and β-alanine-treated glucose oxidase doubly coated with silver (green triangles).

DESCRIPTION OF THE PREFERRED EMBODIMENTS

The present invention is of silver-coated proteins, which substantially retain the biological activity and/or dissolvability of the uncoated protein and can therefore be utilized in various therapeutic applications and in forming electronic circuitry assemblies. The silver-coated proteins according to the present invention are prepared by selectively modifying portions of the protein surface so as to attach a reducing moiety thereto, whereby the reducing moiety participates in an effective, yet controllable in-situ electroless deposition of silver onto the proteins surface, to thereby form the silver-coated proteins. The present invention is therefore further of such modified proteins and of methods of preparing the silver-coated proteins and the modified proteins. The present invention is further of pharmaceutical compositions containing and methods of treating infections utilizing biologically active silver-coated hydrogen-peroxide producing enzymes. The present invention is further of conductive elements comprised of the silver-coated proteins, and of electric circuits and devices containing same. The present invention is further of electrodes having the silver-coated proteins deposited thereon, of biosensors containing same and of uses thereof for electrochemically detecting analytes such as glucose in liquid samples.

The principles and operation of the present invention may be better understood with reference to the figures and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

As discussed hereinabove, electroless deposition is a widely known technique for depositing metals such as, for example, copper, silver and cobalt, on various surfaces. This technique depends upon the reciprocative redox reactions between reducing agents on or adjacent to the subject surface and metal cations in electrolytic solution. During the redox reaction, the metal cations are reduced to their metallic (elemental) state and are deposited onto the subject surface.

As is further discussed hereinabove, electroless deposition have been used to coat (metallize) various biological molecules and particles, yet, it typically resulted in biologically inactive and/or immobilized, insoluble composites. Thus, the highly advantageous ability and utility to deposit metals onto a single, soluble biological moiety, particularly protein, while maintaining its specific biological activity, dissolvability and other characteristic parameters thereof, was not demonstrated hitherto.

Native proteins typically do not promote metal deposition onto their surface. Therefore, while conceiving the present invention, it was envisioned that coating of proteins while retaining their biological activity, dissolvability and other functionally essential features could be achieved by modifying specific sites of the protein surface so as to enable the conjugation of a reducing moiety thereto and utilizing the reducing moiety to affect an electroless deposition of silver onto the protein surface, while overcoming any morphological irregularities which may characterize the surface. It was further envisioned that in order to efficiently utilize such a methodology without affecting the activity or dissolvability of the protein, reducing moieties which can effect silver reduction and deposition mildly, without abolishing the protein biological activity and dissolvability, should be selected. The reduction process should therefore be highly directed and finely controlled with regard to the rates of nucleation and the expansion of the metal deposits at specific sites on the surface of the protein.

While further conceiving the present invention, the present inventors have envisioned that the mild reduction aptitude of reducing moieties such as hydrazines, hydrazides, aldehydes and imines (Schiff-bases), as these terms are defined hereinbelow, could be utilized in the context of the present invention, to affect mild in-situ silver deposition on the surface of a protein.

Thus, while reducing the present invention to practice, the reduction aptitude of the abovementioned reducing moieties was first studied. As is demonstrated in the Examples section that follows, an optimal reduction rate was achieved with hydrazides and imines.

Since reducing moieties such as hydrazides and imines typically do not occur naturally in proteins, the inventors of the present invention have designed and successfully practiced a methodology for introducing such reducing moieties to proteins. This methodology is based on modification of naturally occurring functional moieties on the surface of the subject protein. More specifically, this methodology is based on conjugating reducing moieties such as hydrazides and imines to chemically compatible functional groups on the protein surface and may therefore further include generating such chemically compatible groups. The chemical reactions used to practice such a methodology were selected so as not to affect the protein essential characteristics (e.g., biological activity and dissolvability) and preferably utilize the well known Schiff base chemistry as is detailed in the Examples section that follows.

Hence, as is exemplified in the Examples section that follows, while reducing the present invention to practice, the present inventors have designed and successfully practiced a novel process of preparing modified proteins having reducing moieties attached to their surface, while substantially maintaining the biological activity and dissolvability of the proteins.

As is further demonstrated in the Examples section that follows, such modified proteins were shown to readily undergo a metallization process upon contacting an aqueous solution of silver ions, which resulted in silver-coated proteins. Due to the mild yet potent reducing aptitude of the selected reducing moieties, the biological activity and the dissolvability of the silver-coated proteins was retained.

Thus, according to one aspect of the present invention, there is provided a process of preparing a modified protein and, more particularly, a protein which has a reducing moiety conjugated thereto. As is discussed hereinabove, the modified protein, by virtue of the conjugated reducing moieties, is capable of effecting metal deposition onto at least a portion of its surface, while substantially maintaining its biological activity and/or dissolvability.

Hence, herein throughout, the phrase "modified protein" is used to describe a protein that has been subjected to a chemical modification and, specifically, to modification of at least some of its surface groups, whereby the modification results in conjugation of a reducing moiety to the protein surface. This phrase is therefore used herein to describe a protein that has one or more reducing moieties conjugated to its surface.

Herein, the terms "dissolvable" or "suspendable" and their synonymous term "soluble" are used to describe the capability of a single protein molecule to be dissolved or suspended in an aqueous solution or media.

As used herein, the phrase "reducing moiety" refers to a chemical moiety that is capable of participating in a reduction/oxidation process by either directly or indirectly inducing reduction of other components that participate in such a process. Preferred reducing moieties, according to the present invention, are selected capable of inducing reduction of metal ions into elemental metal atoms. More preferred reducing moieties include functional groups that can affect such a reduction under mild conditions and therefore do not affect functionally essential characteristics of the protein.

The reducing moiety, according to embodiments of the present invention, can be either a functional group, as this term is defined herein, per se, or a chemical group formed by reacting two or more functional groups. As is demonstrated in the Examples section that follows, representative examples of reducing moieties that were found highly suitable for use in the context of the present invention, include, without limitation, hydrazines, hydrazides, and imines (Schiff-bases).

As used herein, the term "hydrazine" describes a —NR'—NR"R'" group, wherein R', R" and R'" are each independently hydrogen, alkyl, cycloalkyl or aryl, as these terms are defined herein.

The term "hydrazide", as used herein, refers to a —C(=O)—NR'—NR'R'" group wherein R', R" and R'" are each independently hydrogen, alkyl, cycloalkyl or aryl, as these terms are defined herein.

The term "Schiff-base", which is also referred to herein and in the art interchangeably as "imine", describes a —N=CR'— group, with R' as defined herein. As is well known in the art, Schiff bases are typically formed by reacting an aldehyde and an amine-containing moiety such as amine, hydrazine, hydrazide and the like, as these terms are defined herein.

The reducing moiety, when conjugated to the protein, can form a part of a chemical moiety that by itself is conjugated to the protein. According to preferred embodiments of the present invention, in cases where the reducing moiety is a functional group such as hydrazine or hydrazide, the functional group forms a part of a chemical moiety as, e.g., an end group or a substituent of the chemical moiety or, alternatively, can be the chemical moiety itself. In cases where the reducing moiety is a Schiff-base, the imine group can be either a substituent or an end group of a chemical moiety, or, alternatively, it is a group that further serves to attach a chemical moiety to the protein surface, as is detailed hereinbelow.

As used herein, the phrase "chemical moiety" describes a chemical compound or a residue of a chemical compound, which typically has certain functionality. As is well accepted in the art, the term "residue" refers herein to a major portion of a molecule which is covalently linked to another molecule.

The chemical moiety is therefore selected such that upon its conjugation to the protein surface, attachment of the reducing moiety to the protein is effected. Thus the chemical moiety can be a bi-functional moiety that includes one functional group that serves for conjugating the moiety to the protein surface (also referred to herein as "a first functional group"), and another functional group which serves as the reducing moiety (also referred to herein as "a second functional group"). Alternatively, the chemical moiety includes a functional group, acting as the first functional group described above, which upon the reaction with the protein surface forms the reducing moiety. Such a chemical moiety, however, can further include an additional functional moiety (the second functional group), which do not participate in the following reduction process but may provide the modified protein with other advantageous properties in the context of the present invention, as is detailed hereinunder. Other features of both the reducing moiety and the chemical moiety according to the present invention are further discussed in detail hereinunder.

The process according to this aspect of the present invention is effected by first providing a protein having one or more reactive groups on its surface; and conjugating to the reactive groups a chemical moiety, whereby the chemical moiety is selected such that upon the conjugation a modified protein having a reducing moiety attached to its surface, is obtained.

As used herein, the phrase "reactive group" describes a chemical group that is capable of undergoing a chemical reaction that typically leads to a bond formation. The bond, according to the present invention, is preferably a covalent bond. Chemical reactions that lead to a bond formation include, for example, nucleophilic and electrophilic substitutions, nucleophilic and electrophilic addition reactions, addition-elimination reactions, cycloaddition reactions, rearrangement reactions and any other known organic reactions that involve a reactive group.

While some of the naturally-occurring proteins have surface reactive groups that are capable of undergoing such chemical reactions under mild conditions and thus may conjugate reducing moieties thereto without affecting the protein essential characteristics, most of the proteins do not have such reactive groups.

Hence, according to a preferred embodiment of this aspect of the present invention, the process is effected by generating such reactive groups on the protein surface, so as to form an activated protein in terms of the reactivity of its surface groups toward the conjugation described herein. The provision of a protein having reactive groups on its surface is therefore also referred to, and described herein, as activation of the protein surface. Preferably, the reactive groups are selected capable of undergoing the conjugation reaction under mild conditions which will not abolish the protein functionally essential characteristics.

According to a preferred embodiment of the present invention, a protein that has reactive groups on its surface is generated while exploiting the presence of naturally occurring functional moieties that bear functional groups, as these phrases are defined hereinbelow, on the protein surface. Providing a protein having reactive groups on its surface is therefore preferably effected by converting a functional group that forms a part of a functional moiety on the protein surface into a reactive group.

As used herein, the phrase "functional moiety" refers to a residue present on the surface of the subject protein, which preferably contains functional groups as defined hereinafter. Exemplary functional moieties, according to the present invention include amino acid residues, as well as post-translationally modified residues such as glycans, lipids, phospholipids, phosphates and the likes.

As used herein, the phrase "functional group" describes a chemical group that has certain functionality and therefore can be subjected to chemical manipulations such as oxidation, reduction, chemical reactions with other components which lead to a bond formation and the like.

A variety of functional groups that can be utilized in the above described conversion are available in proteins. These include, for example, functional groups derived from side chains of certain amino-acid residues, functional groups derived from the N-terminus or the C-terminus of the protein, and functional groups derived from residues that result from natural post-translational modification processes. Representative examples of such functional groups include, without limitation, amine, acyl, aldehyde, alkoxy, thioalkoxy, alkyl, alkenyl, C-amide, N-amide, carboxyl, diol, farnesyl, geranylgeranyl, guanidine, hydroxy, thiohydroxy, imidazole, indole, phosphate and sulfate. These functional groups are also referred to herein as a "third functional group".

As used herein, the term "amine" refers to an —NR'R" group where R' and R" are each hydrogen, alkyl, alkenyl, cycloalkyl, aryl, heteroaryl (bonded through a ring carbon) or heteroalicyclic (bonded through a ring carbon) as defined hereinbelow.

The term "alkyl" as used herein, describes a saturated aliphatic hydrocarbon including straight chain and branched chain groups. Preferably, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, unless otherwise indicated, the alkyl is a lower alkyl having 1 to 5 carbon atoms.

The term "alkenyl" refers to an alkyl group which consists of at least two carbon atoms and at least one carbon-carbon double bond.

The term "cycloalkyl" describes an all-carbon monocyclic or fused ring (i.e., rings which share an adjacent pair of carbon atoms) group where one or more of the rings does not have a completely conjugated pi-electron system. The term "heteroalicyclic" describes a monocyclic or fused ring group having in the ring(s) one or more atoms such as nitrogen, oxygen and sulfur. The rings may also have one or more double bonds. However, the rings do not have a completely conjugated pi-electron system.

The term "aryl" describes an all-carbon monocyclic or fused-ring polycyclic (i.e., rings which share adjacent pairs of carbon atoms) groups having a completely conjugated pi-electron system. The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine.

As used herein, the term "aldehyde" refers to an —C(=O)—H group.

As used in the context of the present invention, the term "diol" refers to a vicinal diol which is a —CH(OH)—CH(OH)— group.

As used herein, the terms "acyl" and "carbonyl" refer to a —C(=O)-alkyl group, as defined hereinabove.

The term "alkoxy" as used herein describes an —O-alkyl, an —O-cycloalkyl, as defined hereinabove.

As used herein, the term "thioalkoxy" describes both a —S-alkyl, and a —S-cycloalkyl, as defined hereinabove.

As used herein, the term "C-amide" refers to a —C(=O)—NR'R" group, where R' and R" are as defined herein.

As used herein, the term "N-amide" refers to an —NR'C(=O)—R" group, where R' and R" are as defined herein.

As used herein, the term "carboxyl" refers to an —C(=O)OR' group, where R' is as defined herein.

The term "farnesyl", as used herein, refers to the fatty residue of fernesene, typically attached to post-translationally modified cysteine residues at the C-terminus of proteins in a thioether linkage (—C—S—C—).

The term "geranylgeranyl", as used herein, refers to the fatty residue of geranylgeranene, typically attached to post-translationally modified cysteine residues at the C-terminus of proteins in a thioether linkage.

The term "guanidine" refers to a —NR'C(=NR")—NR'''R* group, where R' and R" are as defined herein and R''' and R* are defined as either R' or R". In the context of the present invention, guanidine is a functional group on the side-chain of the amino-acid arginine, therefore it is preferably —NH—C(=NH)—NH$_2$.

As used herein, the term "hydroxy" refers to an —OH group.

As used herein, the term "thiohydroxy" refers to an —SH group.

As used herein, the term "imidazole" refers to the five-membered heteroaryl group that includes two non-adjacent nitrogen atoms. An imidazole residue can be found in the side-chain of the amino acid histidine.

As used herein, the term "indole" refers to refers to a bi-cyclic heteroaryl comprised of fused phenyl and pyrrole groups. An indole residue can be found on the side-chain of the amino acid tryptophan.

The term "phosphate" describes a —O—P(=O)(OR')(OR") group, with R' and R" as defined herein. Phosphate groups can be attached to a protein during a post-translational phosphorylation process by kinases. Reversible protein phosphorylation, principally on serine, threonine or tyrosine residues, is one of the most important and well-studied post-translational modifications.

As used herein, the term "sulfate" refers to a —O—S(=O)$_2$—O—R', with R' as defined herein. Modification of proteins with sulfate occurs typically at tyrosine residues, and the universal sulfate donor is 3'-phosphoadenosyl-5'-phosphosulphate.

According to a preferred embodiment of this aspect of the present invention, the reactive group is aldehyde, and the process is effected by providing a protein that has a plurality of aldehyde groups on its surface.

Aldehydes can be readily generated on or introduced to a protein surface, under mild conditions that do not affect the protein nature, using various methodologies well-known and well-described in the art, which are presented briefly hereinbelow.

One of the most common methods for introducing aldehydes to the surface of biological moieties is oxidation, by mild oxidizing agents, of vicinal diols present in glycan residues of glycan-containing proteins. Proteins having glycan residues on their surface (also known as glycoproteins) possess an abundance of diol groups, which readily undergo oxidation to aldehydes using mild oxidizing agents or enzymes.

Thus, according to a preferred embodiment, the protein of choice is a glycoprotein, having functional diol groups that form a part of functional glycan moieties on its surface. According to this embodiment of the present invention, a protein having aldehyde groups on its surface is obtained by oxidizing vicinal diol groups present on the glycan surface residues. The oxidation reaction can be effected in the presence of mild oxidizing agents such as, but not limited to, periodic acid and salts thereof, paraperiodic acid and salts thereof, and metaperiodic acid and salts thereof. An exemplary oxidizing agent that was successfully utilized while practicing this embodiment of the present invention is sodium periodate.

This methodology can further be utilized for generating aldehyde groups on the surface of a lipoprotein. Thus, functional alkenyl residues that form a part of functional moieties such as unsaturated fatty acids, ceramides or other lipids that may be present on a lipoprotein surface can be converted to glycols by osmium tetroxide and subsequently oxidized by any of the oxidizing agents cited above to aldehydes.

Furthermore, functional groups such as hydroxyl groups, that from a part of functional moieties such as N-terminal serine and threonine residues of peptides and proteins can be selectively oxidized by periodate to aldehyde groups.

Alternatively, aldehydes can be introduced to specific cites on a protein surface be means of galactose oxidase. Galactose oxidase is an enzyme that oxidizes terminal galactose residues that are typically present in glycoproteins, to aldehydes. Another common method of introducing aldehydes to the protein surface is by conjugation of a polyaldehyde to chemically compatible functional groups on the protein surface.

As used herein, the term "polyaldehyde" describes a compound that has at least two free aldehyde groups, as this term is defined herein.

A representative example of such a compatible functional group is an amine group, which forms a part of functional moieties such as lysine residues present on the protein surface or the N-terminus of the protein. As is well known and described in the art, conjugation of aldehydes to amine groups that form a part of a protein results in the formation of Schiff bases (imines). This reaction can be carried under mild conditions that do not affect the protein essential characteristics (see, for example, U.S. Pat. No. 4,904,592). When a polyaldehyde is used in such a reaction, one of the free aldehyde groups is reacted so as to form the Schiff base, while at least one aldehyde group remains free yet attached to the amine.

Thus, according to another preferred embodiment of the present invention, a protein having a plurality of aldehyde groups on its surface is obtained by reacting functional groups such as amine groups, which form a part of functional moieties such as lysine residues and/or the N-terminus of the protein with a polyaldehyde. Such a reaction leads to the formation of free aldehyde groups that are attached to the protein surface via imine bonds.

Representative examples of polyaldehydes that are suitable for use in this context of the present invention include glutaraldehyde and its polymeric derivatives, which are referred to herein as polyglutaraldehyde.

Thus, according to the presently most preferred embodiments of the present invention, providing a protein having a plurality of reactive groups such as, for example, aldehydes groups, on its surface is effected by oxidizing functional groups such as diols, which form a part of glycan residues on the surface of a glycoprotein, in the presence of mild oxidizing agent such as periodate. Alternatively, free amine groups that form a part of the side chain of lysine residue and/or of the N-terminus of a protein are reacted under mild conditions with a polyaldehyde so as to attach the polyaldehyde to the protein surface via an imine bond. As is exemplified in the Examples section that follows, using such methodologies, an activated protein that is capable of conjugating thereto a reducing moiety and further retains its biological activity and/or dissolvability can be readily obtained.

It should be noted that an activated protein, which has more than one type of a reactive group can be prepared and utilized in this and other aspects of the present invention. Such an activated protein is prepared by stepwise modifications of functional moieties that are present on its surface, using, for example, the methodologies described hereinabove.

Once an activated protein is provided, a chemical moiety selected so as to form a reducing moiety attached to the protein surface is conjugated to the protein surface. The conjugation is effected between the reactive group(s) on the protein surface and a first functional group that forms a part of the selected chemical moiety.

As is discussed hereinabove, in one embodiment of this aspect of the present invention, the chemical moiety is selected such that the reducing moiety is formed as a result of the conjugation. A representative example of such a reducing moiety is imine, as this term is defined herein, which is typically formed by reacting an aldehyde group and a functional group such as, for example, amine, hydrazine, hydrazide, hydroxylamine, phenylhydrazine, semicarbazide and thiosemicarbazide.

As used herein, the term "hydroxylamine" refers to a —NR'—OH group, where R' is as define herein.

As used herein, the term "phenylhydrazine" refers to an —NR'—NR"R'" group, where R', R" and R'" are as define herein, with at least one of R', R" and R'" being an aryl, as this term is defined herein.

As used herein, the term "semicarbazide" refers to a —NR'—C(=O)—NR"—N R'"R* group, and the term "thiosemicarbazide" refers to a —NR'—C(=S)—NR"—NR"R* group, where R', R", R'" and R* are define herein.

The imine group can be formed, for example, by reacting reactive aldehyde groups that are introduced to the protein surface, as is described in detail hereinabove, with a chemical moiety that includes one or more of the above cited functional groups. Alternatively, the imine group can be formed by reacting a chemical moiety that includes one or more aldehyde groups with one or more of the above cited functional groups that are present and/or introduced to the protein surface. Thus, for example, amine groups that form a part of e.g., lysine residues on the protein surface, can be reacted with an aldehyde, so as to provide an imine-type reducing moiety attached to the protein surface.

As is further discussed in the Examples section that follows, imine groups have been found to act as mild reducing agents of silver.

According to a preferred embodiment of the present invention, the conjugation is effected by reacting a protein that has a plurality of aldehyde groups on its surface, which is preferably obtained as described hereinabove, with a chemical moiety that includes amine as the first functional group. Such a conjugation results in the formation of an imine group, which acts as a reducing moiety.

Chemical moieties having an amine functional group which are suitable for use in this context of the present invention include, without limitation, any alkyl, cycloalkyl, alkenyl or aryl, as these terms are defined herein, that are substituted by at least one amine group or an aminoalkyl group. Such chemical moieties can be further substituted by a variety of substituents, as long as these substituents do not interfere in the formation of the imine reducing moiety or otherwise adversely affect the desired features of the modified protein obtained.

As used herein, the term "aminoalkyl" describes an alkyl group, as this term is defined herein, which is substituted at its end-carbon by an amine group, as this term is defined herein.

According to another preferred embodiment of the present invention, the conjugation is effected by reacting a protein that has a plurality of aldehyde groups on its surface, which is preferably obtained as described hereinabove, with a chemical moiety that includes hydrazine as the first functional group. Such a conjugation also results in the formation of an imine group, which acts as a reducing moiety.

Chemical moieties having a hydrazine functional group which are suitable for use in this context of the present invention include, without limitation, hydrazine per se, as defined herein, or any alkyl, cycloalkyl, alkenyl or aryl, as these terms are defined herein, that are substituted by at least one hydrazine group. Such chemical moieties can be further substituted by a variety of substituents, as long as these substituents do not interfere in the formation of the imine reducing moiety or otherwise adversely affect the desired features of the modified protein obtained.

A representative example of a chemical moiety that has an amine group and which can be efficiently utilized according to the present invention is β-alanine. Such a chemical moiety has an amine group which, when reacted with a protein surface that has a plurality of reactive aldehyde groups, forms an imine that serves as the reducing moiety. As is demonstrated in the Examples section that follows, a modified protein formed by reacting β-alanine and such an activated protein was found to be highly effective in the following reduction process, presumably due to the presence of the anionic carboxylic group that derives from the amino acid moiety. Accordingly, other β-amino acids may be efficiently utilized as chemical moieties in this process.

According to another preferred embodiment of the present invention, the conjugation is effected by reacting a protein that has a plurality of aldehyde groups on its surface, which is preferably obtained as described hereinabove, with a chemical moiety that includes hydrazide as the first functional group. Such a conjugation also results in the formation of an imine group, which acts as a reducing moiety.

Chemical moieties having a hydrazine functional group which are suitable for use in this context of the present invention include, without limitation, hydrazide per se, as defined herein, or any alkyl, cycloalkyl, alkenyl or aryl, as these terms are defined herein, that are substituted by at least one hydrazide group. Such chemical moieties can be further substituted by a variety of substituents, as long as these substituents do not interfere in the formation of the imine reducing moiety or otherwise adversely affect the desired features of the modified protein obtained.

In another embodiment of this aspect of the present invention, the chemical moiety is selected such that the reducing moiety forms a part of the reacting chemical moiety, as a second functional group that does not participate in the conjugation to the protein surface. According to this embodiment, the chemical moiety is conjugated to the protein via another functional group that reacts with the reactive groups on the protein surface. Thus, according to this embodiment of the present invention, the chemical moiety is a bifunctional chemical moiety having one functional group that acts as a reducing moiety and another functional group that serves for conjugating the reducing moiety to the protein, by means of bond formation with the reactive groups on the protein surface.

Preferably, the conjugation of the reducing moiety to the protein surface, according to this embodiment of the present invention, is effected by means of Schiff base chemistry as described hereinabove, such that an aldehyde group is reacted with a chemical moiety that has a functional group such as, for example, amine, hydrazine, hydrazide, hydroxylamine, phenylhydrazine, semicarbazide or thiosemicarbazide.

Thus, as described hereinabove, a protein having aldehyde groups on its surface, which can be obtained as described hereinabove, is reacted with a chemical moiety that has a reducing moiety as one functional group and any of the above cited functional groups as another functional group. Alternatively, a protein having, for example, amine groups on its surface is reacted with a chemical moiety that has a reducing moiety as one functional group and an aldehyde as another functional group.

As is discussed hereinabove and is further demonstrated in the Examples section that follows, preferred functional groups that can efficiently serve as reducing moieties include hydrazines and hydrazides, with hydrazides being the presently most preferred.

Thus, representative examples of preferred chemical moieties that can be used in this context of the present invention include, without limitation, chemical moieties such as alkyl, alkenyl, alkynyl, cycloalkyl and aryl, as these terms are defined herein, which are substituted by at least one hydrazine and/or hydrazide and are further substituted by at least one of amine, hydrazine, hydrazide, hydroxylamine, phenylhydrazine, semicarbazide or thiosemicarbazide. Such chemical moieties can be readily reacted with a protein having a plurality of aldehyde groups on its surface, to thereby attach to the protein surface a reducing moiety.

More preferred chemical moieties that can be used in this context of the present invention include, without limitation, dihydrazides such as, for example, carbonic dihydrazide, oxalic dihydrazide, malonic dihydrazide, succinic acid dihydrazide, glutaric dihydrazide, adipic dihydrazide and heptanedihydrazide. It is assumed that the length of the hydrocarbon chain between the two functional hydrazide groups may affect the yield of the conjugation reaction between the chemical moiety as well as the reduction capacity of the resulting reducing moieties that are attached to the protein surface. A representative chemical moiety that is suitable for use in this context of the present invention is adipic dihydrazide.

According to a preferred embodiment of the present invention, the first functional group is preferably an amine. According to this embodiment, a preferred chemical moiety is β-alanine. As is exemplified in the Examples section that follows, the present inventors have successfully demonstrated the generation of effective reducing moieties onto the surface of proteins, by converting amines and diols that form a part of the protein to aldehydes, and conjugating these aldehydes thereafter to β-alanine. Furthermore, the present inventors have demonstrated the effectiveness of these reducing moieties by allowing the modified proteins containing these reducing moieties to reduce silver ions and thereby obtain silver-coated proteins, which maintained their biological activity and dissolvability. The effective reducing aptitude of the Schiff-base formed between β-alanine and an aldehyde is assumed to be related to the negative charge in the carboxyl group of β-alanine.

According to another preferred embodiment of the present invention, the first functional group is a hydrazide. According to this embodiment, a preferred chemical moiety is adipic-dihydrazide. This chemical moiety is bi-functional, having two hydrazide groups attached thereto. As discussed above, one of the hydrazide groups is utilized as the first functional group which forms an imine by a conjugation reaction with reactive aldehyde groups on the surface of the protein, while the second hydrazide group acts as the second functional group, as defined hereinabove, and introduces an additional reducing moiety onto the surface of the protein.

Using the process described above, modified proteins having one or more reducing moieties attached to the surface thereof are obtained. The chemical nature of the reducing moieties is determined by the chemistry selected for preparing the modified protein, namely, the selected reactive groups and chemical moieties that participate in the process described above. The reducing moieties are selectively attached to the protein surface, at surface positions that bear the reactive groups. Thus, the reduction aptitude of the modified protein can be pre-determined by selecting the desired chemistry applied and, more specifically, by pre-determining the chemistry utilized for generating reactive groups on the protein surface (e.g., modification of lysine or glycan surface residues) and by pre-determining the chemistry utilized for attaching a reducing moiety to the protein (e.g., by virtue of the functional groups in the chemical moiety).

The modified protein according to the present invention can include more than one type of reducing moieties attached thereto. Such a modified protein is obtained by stepwise conjugation of various chemical moieties to the reactive groups on its surface. Alternatively, such a modified protein is obtained by conjugating a chemical moiety to an activated protein that has various reactive groups on its surface.

As is exemplified the Examples section that follows, the present inventors have successfully demonstrated the introduction of effective reducing moieties onto the surface of proteins and have further demonstrated the effectiveness of these reducing moieties by allowing the modified proteins containing these reducing moieties to reduce silver ions so as to obtain silver-coated proteins, which maintained their biological activity and dissolvability.

Hence, according to another aspect of the present invention, there is provided a process of preparing a silver-coated protein. The process according to this aspect of the present invention is effected by contacting an aqueous solution of silver ions with the modified protein described hereinabove. More specifically, the process, according to this aspect of the present invention is effected as follows:

A modified protein having one or more reducing moieties attached to its surface is provided, preferably by the process described hereinabove. The modified protein is dissolved in an aqueous solution and in its biologically active state.

An aqueous solution of silver ions is provided, and the modified protein is brought in contact with the silver ions solution so as to effect reduction of the silver ions into elemental (metallic) silver atoms and thus selective deposition of metallic silver on pre-determined positions on a portion of the protein surface. This process results in deposition of a silver coating on a pre-determined portion of the protein surface, whereby this portion is determined by the functional moieties of the protein surface that are utilized for providing the modified protein and to which the reducing moieties are attached, the density of these moieties on the protein surface and the reduction aptitude of the reducing moieties. The concentration of the silver ions in the aqueous solution depends on the concentration of the modified protein, the density of the reducing moieties on the protein surface, the degree of metallization desired and the relative redox potential (aptitude) of both the metal and the reducing moieties on the protein.

According to a preferred embodiment of this aspect of the present invention, the concentration of the silver ions solution ranges from about 1 mM to 20 mM, and more preferably is about 10 mM.

According to a preferred embodiment of this aspect of the present invention, the molar ratio between the protein and the silver ions ranges from about 1:100 to about 1:1000. The molar ratio is selected in accordance with the characteristics of the subject protein, e.g., the size of the protein, the density of the reducing moieties on its surface, the nature of the reducing moieties and the required coating coverage, as well as the desired rate of metallization.

According to another preferred embodiment of this aspect of the present invention, the silver-coated protein thus obtained can be further reacted so as to form a second, additional silver coating on the protein surface. Thus, according to this embodiment, the silver-coated protein obtained as described above is activated so as to generate additional, second reactive groups on its surface. These additional reactive groups can be either the same reactive groups generated on the (non-coated) protein or different and can be generated using the methodologies described above. The activated silver-coated, which has a plurality of these additional reactive groups on its surface is conjugated to an additional, second chemical moiety, which can be either the same chemical moiety utilized for preparing the silver-coated protein described above or different, so as to form again a (second) reducing moiety attached to the protein surface. Thus, a modified silver-coated protein is obtained, whereby the reactive group, the chemical moiety and the reducing moiety according to this embodiment of the present invention can be any of those described hereinabove for obtaining the modified (non-coated) protein. The modified silver-coated protein is thereafter reacted with an additional (second) aqueous solution of silver ions, so as to form an additional silver coating on the protein surface. The second aqueous solution of silver ions can be the same aqueous solution as described hereinabove or different in terms of its concentration, its chemical characteristics, the molar ratio etc. The resulting silver-coated protein, which has two silver coatings deposited thereon, is also referred to herein as a doubly-metallized or a doubly-coated protein. The coating process described herein can be further repeated so as to provide multiple-coated proteins.

Using the process described hereinabove, a site-directed deposition of metallic silver is effected, and silver-coated proteins that substantially maintain the dissolvability and biological activity characteristics of the protein can be obtained.

Without being bound to any particular theory, it is postulated that the substantial maintenance of the protein biological activity upon the silver deposition process described above may be attributed to the likelihood that the protein is not completely engulfed by the metal coating, but rather has a spotty pattern of silver coverage which does not altogether block biologically-relevant sites on the surface of the protein. Depending on the selected protein, such biologically-relevant sites include, for example, a catalytic reaction active-site of an enzyme, binding and recognition sites for ligands on an antibody, and any other protein-protein or protein-ligand interaction sites of any subject protein.

The process described hereinabove introduces a novel composition-of-matter, which is comprised of the biologically active and/or dissolvable silver-coated protein.

Hence, according to another aspect of the present invention, there is provided a composition-of-matter which includes a protein, characterized by its innate biological activity and dissolvability, having a silver coating deposited over at least a portion of its surface, thus forming a silver-coated protein being dissolvable or suspendable in an aqueous medium, and/or further retaining the biological activity of the native protein.

Being still biologically active, the silver-coated protein can form a part of a cell or other intra-cellular systems, or any other biological system, such as, but not limited to serum, plasma and other extra-cellular systems.

The deposited silver coating on the surface of the protein covers at least a portion of the protein surface. As used herein, the term "at least a portion" describes a certain portion of the protein, which is determined as described hereinabove. This portion can range from about 0.01% of the protein surface to substantially all the protein surface. According to a preferred embodiment of the present invention, the silver-coating on the surface of the protein covers from about 0.1% to about 60% of the solvent-accessible surface of the protein.

The silver coating can be either in the form of a continuous metallic silver layer, covering parts or all of the surface, or in the form of one or more separate silver particles deposited on one or more sites of the protein surface.

Depending, at least in part, on the reducing moiety used, the deposited metallic silver may be in a crystalline form, having a well-ordered structure. Alternatively, the deposited metallic silver is in an amorphous form. Preferably, the deposited silver has a crystalline form, which is highly suitable, for example, for applications where electronic conductivity is desired.

The size of a single deposited metallic silver particle may range from about 1 nanometer to about 30 nanometers in diameter. A micrograph of a portion of an exemplary silver-coated protein according to the present invention is presented in FIG. 4, and shows a patch of about 11 nm in diameter of crystalline silver deposited on the surface of a protein.

According to the abovementioned aspects of present invention, the metal deposition transpires in-situ on the surface of the subject protein requiring a reducing moiety attached to the surface thereof. Therefore, according to a preferred embodiment of this aspect of the present invention, the surface of the silver-coated protein described herein includes one or more oxidized reducing moieties, either near or underneath the metal particle. During the deposition of the silver onto the protein surface, the silver ions are reduced to metallic silver whereby the reducing moieties are oxidized.

In any of the aspects of the present invention described above, the utilized protein can be any naturally occurring or modified protein including, but not limited to, an antibody (including fragments thereof), a lectin, a nucleic acid binding protein, a cellular protein, a serum protein, a growth factor, a hormone, an enzyme, a glycoprotein and a transcription factor, all are characterized by solubility in aqueous media and a specific biological activity.

It is assumed that in some cases, other types of proteins, which in their native form are attached to an insoluble matrix or otherwise immobilized, can be partially coated with metal according to some aspects of the present invention, and still maintain their biological activity. Such proteins may include proteins of the intra- and extra-cellular matrices, membranal proteins such as receptors and channels, fibrous proteins and fragments thereof.

According to a preferred embodiment of the present invention, the protein is an enzyme and the composition-of-matter comprises a silver-coated enzyme, which is characterized by being dissolvable in an aqueous medium, and by retaining its specific biological catalytic activity.

As is exemplified in the Examples section that follows, silver-coated enzymes and, more specifically, silver-coated glucose oxidase and horseradish peroxidase, were successfully prepared using the methodologies described hereinabove. The silver-coated enzymes were assayed for their residual specific activity and dissolvability after each step of the process and were shown to retain a significant level of these characteristics, as compared with their activity prior to any modification, after the activation process, through the introduction of reducing moieties thereto, and after the deposition of a silver coating on at least a portion of their surface.

Hence, according to a preferred embodiment of the present invention, the proteins onto which a silver-coating is applied are the enzymes glucose oxidase and horseradish peroxidase. For general information regarding these enzymes, see the Examples section that follows.

Silver, in its metallic or ionic state, is known as a useful agent in various medicinal applications. These include topical treatment of wounds (an exemplary commercial product is the FDA approved anti-microbial preparation Silverlon® by Argentum Medical, LLC) and controlled prophylaxis of severe burns (using silver sulfadiazine).

Hydrogen peroxide is also well known as an anti-microbial and anti-bacterial agent and thus is widely used in the treatment of infections and in various medicinal and industrial applications.

The present inventors have thus envisioned that the anti-microbial activity of silver may be beneficially utilized by coating biologically active biological moieties such as proteins. The present inventors have further envisioned that such an activity can be enhanced when the coated protein is further associated with the production of hydrogen peroxide, such that a synergistic effect would result by combining the biological activity of the protein, and the anti-microbial activity of both the silver and the hydrogen peroxide.

The synergism between hydrogen peroxide and silver has already been harnessed for the production of environmentally friendly biocides for the effective control of water borne micro-pathogens including *Legionella, E. Coli, Pseudomonas, Cryptosporidium, Campylobacter, Salmonella*, methicillin resistant *Staphylococcus Aureus*, vancomycin resistant *Enterococcus* and other bacterial, viral and fungal infections. An example for such a product is the commercially available water treatment agent Accepta-8101 by Accepta Ltd. of England.

Combining the anti-microbial activity of silver and hydrogen peroxide along with the biological activity of a protein can be achieved, using the methodologies described herein, by depositing a silver coat on a hydrogen-peroxide producing enzyme, while maintaining the biological activity and/or dissolvability of the enzyme.

Thus, according to a preferred embodiment of the present invention, the protein utilized in each of the aspects described hereinabove is a hydrogen peroxide producing enzyme.

As used herein and is well known in the art, hydrogen peroxide producing enzymes are enzymes which catalyze reactions during which hydrogen peroxide is generated. Representative examples of such enzymes include, without limitation, glucose oxidase, oxalate oxidase and superoxide dismutase.

The preparation of biologically active silver-coated hydrogen producing enzymes using the methodologies described herein may therefore be beneficially utilized in the treatment of bacterial and/or fungal infections. As is delineated hereinabove, such silver-coated enzymes are capable of exerting a synergistic effect as a result of the generation of hydrogen peroxide, an anti-microbial agent by itself, which may further act as an oxidizing agent that may oxidize the metallic silver deposited on the enzyme and thus generate free silver ions. The released silver ions and the generated hydrogen peroxide may thus act synergistically as toxic agents against various bacteria, fungi and other microorganisms.

Hence, according to another aspect of the present invention, there is provided a method of treating bacterial and/or fungal infections. The method, according to this aspect of the present invention, is effected by administering to a subject in need thereof a therapeutically effective amount of a composition-of-matter including a silver-coated hydrogen producing enzyme, as described hereinabove.

As used herein, the terms "treating" and "treatment" includes abrogating, substantially inhibiting, slowing or reversing the progression of a condition, substantially ameliorating clinical or aesthetical symptoms of a condition or substantially preventing the appearance of clinical or aesthetical symptoms of a condition.

As used herein, the phrase "therapeutically effective amount" describes an amount of the composite being administered which will relieve to some extent one or more of the symptoms of the condition being treated.

In one preferred embodiment of the present invention, the therapeutically effective amount for the silver-coated enzymes ranges from about 0.1 mg to about 50 mg per one ml of a medium.

According to a preferred embodiment of this aspect of the present invention, the substrate of the hydrogen peroxide producing enzyme is a vital food source, such as sugars, or other metabolites crucial for the survival of the target bacteria or fungi. Using such an enzyme provides an additive effect since depleting a vital source that is required for the bacteria or fungi growth further results in growth inhibition thereof. Hence, altogether, using such a silver-coated enzyme results in a triple action against infectious microorganisms: a toxic effect exerted by the hydrogen peroxide produced during the enzymatic catalysis of the enzyme, a toxic effect exerted by silver ions that are released when the silver-coated enzyme interacts with the produced hydrogen peroxide, and a growth inhibition of the microorganisms that results from depleting a vital source thereof.

Thus, preferred silver-coated enzymes according to this aspect of the present invention are silver-coated hydrogen peroxide producing enzymes that act on a substrate that serves as a vital source for microorganism growth. An example for such a substrate is sugar, e.g., glucose. A preferred enzyme for use in this context is therefore a hydrogen-producing enzyme that uses glucose as a substrate. An exemplary and preferred enzyme, according to this aspect of the present invention, is glucose oxidase.

As is demonstrated in the Examples section that follows, the present inventors have successfully utilized a silver-coated glucose oxidase to inhibit the growth of bacteria and fungi. Thus, silver-coated glucose oxidase, prepared using the methodologies of the present invention described hereinabove, was found to be highly effective in inhibiting the growth of *Staphylococcus aureus, Bacillus megaterium* and *Escherichia coli*.

The silver-coated enzymes described herein, alone or in combination with any other active agents, can be utilized in this or any other aspect of the present invention either per se, or as a part of a pharmaceutical composition.

Hence, according to still another aspect of the present invention, there are provided pharmaceutical compositions, which comprise the composition-of-matter described above and a pharmaceutically acceptable carrier. In one embodiment of this aspect of the present invention, the pharmaceutical composition comprises a composition-of-matter that includes a silver-coated hydrogen peroxide producing enzyme and is identified for use in the treatment of bacterial and fungal infections.

As used herein a "pharmaceutical composition" refers to a preparation of the silver-coated enzyme described herein, with other chemical components such as pharmaceutically acceptable and suitable carriers and excipients. The purpose of a pharmaceutical composition is to facilitate administration of a compound to an organism.

Hereinafter, the term "pharmaceutically acceptable carrier" refers to a carrier or a diluent that does not cause significant irritation to an organism and does not abrogate the biological activity and properties of the administered compound. Examples, without limitations, of carriers are: propylene glycol, saline, emulsions and mixtures of organic solvents with water, as well as solid (e.g., powdered) and gaseous carriers.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences" Mack Publishing Co., Easton, Pa., latest edition, which is incorporated herein by reference.

Pharmaceutical compositions for use in accordance with the present invention thus may be formulated in conventional manner using one or more pharmaceutically acceptable carriers comprising excipients and auxiliaries, which facilitate processing of the silver-coated enzymes into preparations which, can be used pharmaceutically. Proper formulation is dependent upon the route of administration chosen. Toxicity and therapeutic efficacy of the silver-coated enzymes described herein can be determined by standard pharmaceutical procedures in experimental animals, e.g., by determining the $EC_{50}$, the $IC_{50}$ and the $LD_{50}$ (lethal dose causing death in 50% of the tested animals) for a subject silver-coated enzyme. The data obtained from these activity assays and animal studies can be used in formulating a range of dosage for use in human.

The dosage may vary depending upon the dosage form employed and the route of administration utilized. The exact formulation, route of administration and dosage can be chosen by the individual physician in view of the patient's condition. (See e.g., Fingl et al., 1975, in "The Pharmacological Basis of Therapeutics", Ch. 1 p. 1).

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA (the U.S. Food and Drug Administration) approved kit, which may contain one or more unit dosage forms containing the active ingredient. The pack may, for example, comprise metal or plastic foil, such as, but not limited to a blister pack or a pressurized container (for inhalation). The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions for human or veterinary administration. Such notice, for example, may be of labeling approved by the U.S. Food and Drug Administration for prescription drugs or of an approved product insert. Compositions comprising a silver-coated enzyme of the invention formulated in a compatible pharmaceutical carrier may also be prepared, placed in an appropriate container, and labeled for treatment of an indicated condition or diagnosis, as is detailed hereinabove.

Thus, according to an embodiment of the present invention, depending on the selected components of the silver-coated enzymes, the pharmaceutical compositions of the present invention are packaged in a packaging material and identified in print, in or on the packaging material, for use in the treatment of bacterial and/or fungal infections, as described hereinabove.

The electronic conductive nature of the silver deposited on the silver-coated proteins described herein, along with the biological specificity typically associates with biological active proteins, can be further harnessed in the construction of various conductors and semiconductors elements. The ability to combine the nano-size metal particles deposited on a biologically active protein, and the natural molecular recognitions and highly-specific chemical binding capacities of proteins, presents an opportunity to develop nano- and micro-sized electronic circuit assemblies which are assembled by using, partially or entirely, the natural affinity of proteins to other proteins and ligands. As used herein, the term "nano-size" refers to a size magnitude that ranges from 1 nm to 1000 nm.

Hence, according to yet another aspect of the present invention, there is provided a conductive element which includes the composition-of-matter described above. The conductive element, according to this aspect is of a size magnitude which ranges between 1 and 1000 nanometer.

These conductive element based on silver-coated proteins can be used, according to a preferred embodiment of the present invention, in the construction of electronic circuit assemblies comprising an arrangement of conductive elements interconnecting many other electronic elements wherein some are the composition-of-matter described above.

The composition-of-matter described herein can be further utilized in the construction of biosensors.

As discussed hereinabove, there is a need for accurate, sensitive and low-cost biosensors, which are based on electrodes having a redox enzyme attached thereto, for the determination of an analyte in a sample. For example, micro- and nano-electrodes for the quantitative and qualitative detection of glucose is an important technological goal on the path to produce small and low-cost glucose meters which are in high demand as medical and research devices. The presently known systems that utilize glucose oxidase in bio-electrodes aimed at detecting glucose concentrations in a sample are typically prone to high noise level and interferences from other electro-oxidizable species. Other systems involve the cost-ineffective use of bi-enzymatic systems.

As is further discussed hereinabove, in cases where an "oxygen deficit" adversely affects electrochemical detection of analytes, synthetic mediators are advantageously introduced to the system. However, while ferrocene (Fc) and derivatives thereof have been widely used as mediators for that purpose, their poor absorption on the electrode surface often limits the process efficiency.

Recently, it has been shown [Scholz, F. and Hasse, U., *Electrochemistry Communications*, 7:541-546, 2005] that electrochemical connection between Fc and metallic silver leads to preservation of high levels of Fc+ near the electrode surface, without the need to physically attach the Fc mediator. In addition, metallic silver may participate in an electrochemical reaction with Fc, as follows:

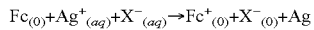

$Fc_{(0)} + Ag^+_{(aq)} + X^-_{(aq)} \rightarrow Fc^+_{(0)} + X^-_{(0)} + Ag$

This reaction has a negative standard free energy and therefore proceeds spontaneously. Applying a voltage increases the rate of the reaction by promoting the electron transfer from the mediator to the metal ions. This study argues that silver crystals located at the interface between two liquid phases act as bipolar electrodes, where silver ions were discharged and Fc was oxidized.

In order to achieve high sensitivity and stability, it is crucial to ensure immobilization of the enzyme(s) and to maintain close contact between the enzyme(s), the mediator and the electrode surface.

While further reducing the present invention to practice, an electrochemical biosensor system capable of quantitatively and qualitatively detecting glucose was constructed and successfully practiced, as demonstrated in the Examples section that follows. This glucose detecting biosensor is based on an electrode having a silver-coated glucose oxidase deposited thereon and is further based on the amperometric electrochemical measurement of the current resulting from the electrochemical oxidation or reduction of an electroactive species at a constant applied potential.

Thus, according to another aspect of the present invention there is provided an electrode which comprises a composition-of-matter as described herein being deposited thereon.

The electrode having the composition-of-matter deposited thereon is referred to herein as the working electrode, as this term is commonly used in the art. The basis of the working electrode, according to the present invention, can be any commercially available or specially prepared working electrode. The most commonly available working electrodes are carbon-based, such as, for example working electrode made of glassy carbon, pyrolytic carbon and porous graphite. Working electrode based on metals, such as, for example, platinum, gold, silver, nickel, mercury, gold-amalgam and a variety of alloys, can also be used as working electrode according to the present invention.

Preferably the working electrode is a carbon-based working electrode, as is further detailed hereinbelow.

The composition-of-matter can be deposited onto the working electrode by means of, for example, a sol-gel film, a polymer film, a cross-linking agent and/or other protein immobilization techniques known in the art. Preferably the immobilization of the composition-of-matter is effected by a cross-linking process using glutaraldehyde as a cross-linking agent. The cross-linked structure prevents the composition-of-matter presented herein from eluting into a liquid sample.

The electrode described herein can be utilized for constructing a biosensor system for electrochemically detecting analytes in a liquid sample.

As used herein throughout, the term "detecting" encompasses qualitatively and/or quantitatively determining the level (e.g., concentration, concentration variations) of an analyte in the sample.

Hence, according to another aspect of the present invention there is provided a biosensor system for electrochemically determining a level of an analyte in a liquid sample, which comprises an insulating base and an electrode system. The electrode system, according to the present invention, includes the abovementioned working electrode, whereby the composition-of-matter described herein comprises a silver-coated protein which is capable of reacting with the analyte (e.g., a substrate) while producing a transfer of electrons.

The biosensor presented herein is based on typical biosensors known and used in the art, and includes an electrodes system in an insulating base. The electrodes system, preferably made of carbon electrodes, includes a working electrode having the composition-of-matter presented herein deposited thereon, and a counter (also referred to as an auxiliary electrode) electrode. The electrode system can further include a reference electrode, such as, for example, a saturated calomel electrode.

As in typical biosensors, when the biosensor is placed in contact with a liquid sample containing the analyte, the analyte electrochemically reacts with silver-coated protein deposited on the working electrode, so as to produce a transfer of electrons (en electric current). The presence and magnitude of the electric current, which is proportional to the concentration of the analyte in the liquid sample, is recorded by the system.

FIG. 6 illustrates a biosensor which includes the electrode of the present invention held in place by an insulating base. Biosensor 10 comprises an insulating base 12 which includes a working electrode 14, a reference electrode 24 and a counter electrode 22. Working electrode 14 is fabricated from any conducting material, preferably carbon, platinum or gold, as discussed hereinabove, and has a plurality of metal-coated proteins 16, as described above, deposited thereon; reference electrode 24 and counter electrode 22 are similar in type and composition to electrodes known in the art.

Counter electrode 22 is typically fabricated from conducting material and typically has a higher surface area than that of working electrode 14. All three electrodes can be fabricated via extrusion, stamping, casting or the like of a conductor (e.g., metal) or by depositing/printing the metal on an inert substrate such as silicon oxide using methodology well known in the art such as, for example, screen-printing.

Biosensor 10 further comprises a detecting unit 20 (e.g., potentiostat/amperometer) which is electrically connected (indicated by 18) to electrode 14, reference electrode 24 and counter electrode 22 held in place by insulating base 12. Detecting unit 20 is capable of detecting and presenting a response current generated by electrode 14.

The biosensor of the present invention can include any of the compositions-of-matter described herein, as long as the protein in the composition-of-matter can react with an analyte and the reaction can be electrochemically detected. Preferred compositions-of-matter, however, are those containing an enzyme as the silver-coated protein and more preferably an oxidoreductase (redox) enzyme.

The term "analyte" as used herein refers to a substance that is being analyzed for its level, namely, presence and/or concentration, in a sample. An analyte is typically a chemical entity of interest which is detectable upon an electrochemical reaction and which the biosensor presented herein is design to detect. Examples of analytes that are typically detectable by biosensors include, without limitation, enzyme substrates. A level of an enzyme substrate analyte in a sample is determined by biosensors that include silver-coated enzymes, whereby this level is a function of the electric current produced upon the enzymatic reaction.

The term "redox" as used herein refers to a chemical reaction in which an atom in a molecule or ion loses one or more electrons to another atom or ion of another molecule.

The phrase "oxidoreductase enzyme", which is also referred to herein interchangeably as "redox enzyme" describes an enzyme which catalyzes a reaction that involves the transfer of electrons from one molecule (the oxidant, also called the hydrogen donor or electron donor) to another molecule (the reductant, also called the hydrogen acceptor or electron acceptor), or, in short, catalyzes a redox reaction. Examples of redox enzymes include, without limitation, glucose oxidase, glucose dehydrogenase, lactate oxidase, lactate dehydrogenase, fructose dehydrogenase, galactose oxidase, cholesterol oxidase, cholesterol dehydrogenase, alcohol oxidase, alcohol dehydrogenase, bilirubinate oxidase, glucose-6-phosphate dehydrogenase, amino-acid dehydrogenase, formate dehydrogenase, glycerol dehydrogenase, acyl-CoA oxidase, choline oxidase, 4-hydroxybenzoic acid hydroxylase, maleate dehydrogenase, sarcosine oxidase, uricase, and the like.

When using a biosensor based on a hydrogen peroxide-producing enzyme to measure an analyte which is a substrate thereof, the oxidation current of $H_2O_2$ is usually proportional to the concentration of the analyte in solution and is detected at +700 mV versus a reference electrode. However, as mentioned above, monitoring hydrogen peroxide is limited by the presence of substances such as ascorbic acid and uric acid, which are electroactive at similar voltages and are abundant in physiological samples, such as blood serum, and would therefore interfere with amperometric transducers based on the $O_2/H_2O_2$ electron-transfer mediator system.

In order to overcome these limitations, non-physiological electron transfer mediators such as, for example, phenazines, tetrathiafulvalene (TTF), ferrocenes, ferrocyanides, quinones, fullerenes and ruthenium complexes are used, as is detailed hereinabove. Thus, the biosensor system presented herein preferably further comprises an electron transfer mediator (also referred to herein as a mediator). Preferably the mediator is a ferrocene derivative, and more preferably the mediator is ferrocene monocarboxylic acid.

While, as discussed hereinabove, the use of ferrocenes in biosensors is often limited by their poor absorption to the electrode, by using biosensors that are based on silver-coated proteins, this limitation is circumvented, as is detailed hereinabove.

Generally, all proteins, preferably enzymes and more preferably redox enzymes, can undergo the treatment of metallization as presented herein and exemplified in the Examples section that follows, and be coated with a single or multiple coats of a metal, such as silver, so as to form a coat of crystalline or amorphous silver thereon.

Preferably, the composition-of-matter deposited on the electrode used in the biosensor presented herein includes glucose oxidase, and hence the biosensor is preferably used for determining the level of glucose in a liquid sample.

Use of the silver-coated enzyme presented herein, such as, for example, singly silver-coated and/or doubly silver-coated glucose oxidase which includes an active enzyme having lysine-bound polyglutaraldehyde coupled to β-alanine residues, offers several added advantages to an electrochemical system. These include, for example, stabilization of the silver-coated enzyme by its cross-linking with polyglutaraldehyde, hence prolonging the time of effective use of the electrode, and providing additional "wiring" between the silver coated enzyme and the electrode. In addition, the crystalline morphology of the silver coating of the enzyme provides a continuous contact surface between the enzyme and the working electrode, providing shorter distance for the ferrocene mediator to shuttle its electrons. Hence, another key advantage gained by using the silver-coated enzymes of the present invention for electrochemical electrodes is a significant increase in the total surface area of the electrode, as each silver-coated glucose oxidase molecule may be considered as an individual nano-electrode.

Therefore, according to preferred embodiments, the protein in the composition-of-matter is the enzyme glucose oxidase.

As is demonstrated in the Examples section that follows, electrodes having silver-coated glucose oxidase were found to be particularly efficient when a doubly silver-coated enzyme with a crystalline form of silver was utilized. Thus, in preferred embodiments, the composition-of-matter deposited on the electrode comprises a doubly-silver coated enzyme and further preferably, the silver coat has a crystalline morphology.

The biosensor presented herein is therefore designed for detecting an analyte in a sample, which can be, for example, a physiological sample extracted from an organism. Hence, according to another aspect of the present invention there is provided a method of electrochemically determining a level of an analyte in a liquid sample. The method, according to this aspect of the present invention, is effected by contacting the biosensor system presented herein with the liquid sample and measuring the transfer of electrons formed upon the electrochemical reaction between the analyte and the silver-coated protein, thereby determining the level of the analyte substrate in the sample. Use of a reference and/or use of a set of known standard samples with known concentrations can be used to convert the amperometric results into concentration of the analyte in the sample.

Preferably, the method presented herein is used for determining the level of glucose in a liquid sample, while utilizing silver-coated glucose oxidase.

However, by selecting a protein that can electrochemically react with an analyte so as to produce a transfer of electrons, and depositing such a silver-coated protein on a working electrode in a biosensor system, the systems and methods described herein can be further utilized for determining levels of versatile analytes.

Thus, several other important biochemical analytes can also be readily detected using the biosensors presented herein. Non-limiting examples include a biosensor for lactate using metal-coated lactate dehydrogenase, a biosensor for bilirubin using metal-coated bilirubin oxidase, and a biosensor for amino acids and peptides using metal-coated amino acid oxidase and tyrosinase. Other examples of enzymes which can be utilized by present invention are provided in Table 1 below, presenting the name of the enzyme which also indicates the analyte, i.e., substrate thereof, the chemical species that is formed in the course of the enzymatic reaction, and a typical exemplary use of the biosensor which can be constructed using these enzymes.

technique of a silver-coated enzyme based electrode which can be used for a glucose-determining electrochemical system.

Such glucose-determining electrochemical system can be based on disposable and multi-arrayed screen-printed electrodes assisted by synthetic mediators such as ferrocene that can react rapidly with the reduced enzyme, and minimize competition with oxygen and other electro-oxidizable species. Screen-printing technology is particularly attractive for the production of disposable sensors, such as for determining glucose levels [Ge, F., et al., Biosens Bioelectron. 1998, 1; 13(3-4):333-9]. The "memory effect" between one sample to another is avoided, and, the phenomenon referred to as "electrode fouling", which is one of the main drawbacks of the electrochemical sensors, is overcome. Furthermore, these disposable sensors are characterized by high reproducibility and require no calibration.

Screen-printed electrodes are particularly useful in high-throughput screening (HTS) and ultra-high throughput screening (UHTS) technology. Their small size and low cost permit HTS/UHTS of large numbers of electrochemical assays to be conducted simultaneously, at minute volumes of microbiological and/or biochemical samples, using disposable, screen-printed electrochemical microarrays.

TABLE 1

| Enzyme/Ligand | Molecule generated or captured | Use |
| --- | --- | --- |
| Peroxidase | Hydrogen peroxide | Immunology, medicine Environment |
| Glucose oxidase | Glucose | Medicine, Food industry |
| Alcohol oxidase | Alcohol | Food, medicine, police |
| Cholestrol oxidase | Cholesterol | Medicine, food |
| Choline oxidase | Choline, acetyl choline | Medicine, environment, anti-warfare detector |
| Phenol oxidase | Phenol | Medicine, food, environment |
| Aminoacid oxidase | Amino acids | Medicine |
| Alcohol dehydrogenase | Alcohol, NAD | Food, medicine, police |
| Glucose dehydrogenase | Glucose, NAD | Medicine, Food industry |
| α and β-Glactosidase | Lactose, p-aminophenol -D galactopyranoside | Food, molecular biology, cell markers, medicine, detection of bacteria |
| α and β Glucosidase | Glucose, p-aminophenol -D glucopyranoside | Food, molecular biology, cell markers, medicine, detection of bacteria |
| α and β Glucoronidase | Glucoronic acid, p-amino-phenol -D glucoronopyranoside | Food, molecular biology, cell markers, medicine, detection of bacteria |
| Alkaline phosphatase | Organic phosphate | Immunology, Food, molecular biology, cell markers, medicine, detection of bacteria |

The biosensors presented herein can be further utilized for monitoring of drugs. Such biosensors include, for example, a biosensor for theophylline using metal-coated theophylline oxidase. In addition to medical applications, biosensors based on the metal-coated redox enzymes presented herein can be used in food technology and biotechnology, e.g., for analysis of carbohydrates, organic acids, alcohols, additives, pesticides and fish/meat freshness, in environmental monitoring, e.g., for analysis of pollutants pesticides, and in defense applications, e.g., for detection of chemical warfare agents, toxins, pathogenic bacteria and the likes.

As presented and demonstrated in the Examples section that follows, a silver-coated enzyme was readily absorbed into the screen-printed carbon ink-working electrode. The method presented in the Examples section that follows provides a fast and convenient immobilization and fabrication Thus, according to preferred embodiments, the electrode used in the glucose biosensor is a screen-printed electrode.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Materials and Experimental Methods:

Enzymes:

Glucose oxidase from *Aspergillus niger* (cat no. G-2133), and peroxidase from horseradish (cat. no. P-8250), purchased from Sigma, were selected as exemplary proteins in this study.

Horseradish peroxidase (HRP) is a 40,000 kD molecular weight glycoprotein that interacts with hydrogen peroxide and specific electron donors, such as ascorbic acid, L-cysteine and reduced glutathione, and catalyzes the oxidation of various substrates. This enzyme has an optimal activity at pH 7.6 and is known to be inhibited by cyanides, sulfides and azides [Murachi, T. et al. (1980), *Biochimie* 62(8-9): 581-5].

Glucose oxidase from *Aspergillus niger* catalyzes the oxidation of β-D-glucose, producing hydrogen peroxide ($H_2O_2$) and gluconic acid. Glucose oxidase is a dimeric glycoprotein with a molecular weight of 160,000 kD. Inhibitors of glucose oxidase include metal ions, p-chloromercuribenzoate and phenylmercuric acetate [Murachi, T. et al. (1980), *Biochimie* 62(8-9): 581-5].

The analytical and medicinal importance of these enzymes has been well recognized [see, for example, R. Wilson and A. P. F. Turner, *Biosensors & Bioelectronics* 1992, 7, pp. 165-185; and N. C. Veitch, *Phytochemistry* 2004, 65, pp. 249-259]. Both enzymes are glycoproteins having known glycans on their surfaces, and are characterized by high stability in their isolated and purified form.

Metal:

Silver was selected as an exemplary metal in view of its abundant and successful use in protein metallization [see, for example, W. Habicht et al. in *Surf. Interface Anal.* 2004, 36, pp. 720-723].

Silver nitrate (cat. no. 5553260) was purchased from Frutarum.

Reagents:

Glyceraldehyde (cat. no. G-5001), β-Alanine (cat. no. A-7752), and sodium periodate (cat. no. S-1147) were purchased from Sigma. Adipic-dihydrazide (cat. no. 217824) and formic hydrazide (cat. no. 166375) were purchased from Aldrich. Glutaraldehyde (cat. no. 1.04239), and ammonia solution (cat. no. 1.05432) were purchased from Merck. 2-Diethylaminoethylamine (cat no. 21228) was purchased from Fluka. N,N-diethyl ethylenediamine (cat. no. 31790) was purchased from Fluka. Hydrazine (cat. no. 20.794-2) was purchased from Aldrich.

Microorganisms:

*Staphylococcus aureus* (wile-type SH 1000) was obtained from the laboratory of Prof. Y. Aharonowitz, Department of Molecular Microbiology and Biotechnology, Tel Aviv University, Tel-Aviv, Israel, *Candida albicans* and *Trichophyton rubrum* were obtained from Dr. R. Segal, Rabin Hospital, Petach-Tikva, Israel, *Bacillus megaterium* (de Bary) was purchased from American Type Culture Collection (ATCC 13368) and *Escherichia coli* (wild-type MG 1655 K12) was obtained from Dr. I. Benhar, Department of Molecular Microbiology and Biotechnology, Tel Aviv University, Tel-Aviv, Israel.

High Resolution Transmission Electron Micrographs (HR-TEM):

Electron micrographs of the silver particles in solution and on the surface of the metallized enzymes were obtained by a high resolution electron microscope (Philips Tecnai F20) without further staining.

Spectrophotometric Measurements:

The variation in optical density, generated by the turbidity of the solid silver precipitations after reduction of silver nitrate, was measured using a spectrophotometer operated at a wavelength of 450 nm. Bacterial growth was measured by an Ultrospec 2100 spectrophotometer (Amersham), operated at a wavelength of 600 nm.

Preparation of an Enzyme Having a Reducing Moiety Conjugated Thereto-General Description:

The main objective of the studies described below was to deposit a metal coating, and particularly silver coating, on the surface of an enzyme with minimal impact on the enzyme's biological activity and dissolvability. Such a deposition on a surface of an active enzyme requires highly directed and finely controlled rates of nucleation and the expansion of the reduction processes of the metal deposits at specific sites.

To direct and control such nucleation and expansion of metal deposition, the novel process of the present invention for protein metallization is based on the conjugation, to specific sites on the protein surface, of specific reducing moieties, under mild and controllable physiological conditions; non-denaturing removal of excessive unbound reagents; and non-denaturing incubation of the modified enzyme with ions of the desired metal.

The present inventors have hypothesized that the mild reduction aptitude of reducing moieties such as hydrazines, hydrazides, aldehydes and imines (Schiff-bases) could be utilized in the context of the present invention, to affect in situ silver deposition on the surface of a protein. Since these reducing moieties do not occur naturally in most proteins, they must be introduced to the protein by either conversion of and/or conjugation to naturally occurring functional groups on the surface of the subject protein. It was further hypothesized that aldehydes, which can be readily introduced to proteins, may serve as suitable reactive groups which interact under mild conditions, and thus may be utilized for conjugating versatile chemical moieties so as to form a reducing moiety on the surface of the protein. Aldehydes may be generated on the surface of a protein by converting various surface functional groups thereof, or be attached to surface functional groups by means of bi-functional chemical moieties, as described in detail below.

As a representative example for a suitable conjugation method in non-denaturing conditions, the well established Schiff-base (imine) formation between amines and aldehydes has been selected (see, Scheme I below). This universal conjugation method can be carried out readily under physiological, i.e., mild conditions, as described by Merril et al. [*Science*, 1981, 211, pp. 1437-1438].

Scheme 1

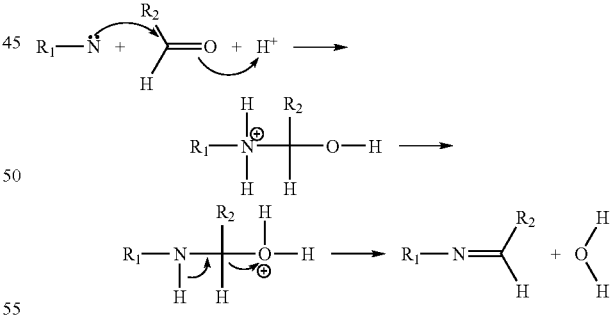

Thus, Schiff-base chemistry may be applied, for example, by conjugating an aldehyde or a ketone to naturally occurring amine groups present on the surface of a protein, such as in lysine residues and the N-terminus; by conjugating an amine, a hydrazine or a hydrazide to aldehyde groups generated on the glycoprotein surface by periodate oxidation of some or all of the diol groups in the glycan structure (see, Scheme 2 below); and/or by conjugating an amine, a hydrazine or a hydrazide to aldehyde groups introduced to the enzyme by treatment with bi- or multifunctional reagents such as glutaraldehyde and its polymerization derivatives.

Scheme 2

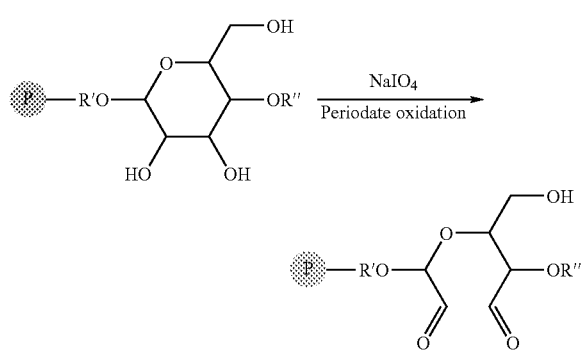

P represents a glycoprotein; and R' and R'' each represents a part of a glycan residue.

venient conjugation capabilities to the protein surface through the spacer.

The reduction reaction in solution was measured by the differences in the optical density at 450 nm ($\Delta OD_{450}$) of the solution, before and after the addition of a reducing agent.

The tested solutions were prepared by adding 1 ml of a 12 mM solution of silver nitrate to:

0.42 ml of a 0.25 M solution of hydrazine (HH);

0.42 ml of a 0.25 M solution of formic hydrazide (FH); and 0.42 ml of a 0.25 M solution of adipic dihydrazide (ADH).

Hence, the final concentration of silver nitrate was 4 mM, and the final concentration of each reducing agent was 35 mM.

Table 2 below presents the results obtained in these measurements.

TABLE 2

| No. | Reducing moiety | $\Delta OD_{450}$ | | | | |
|---|---|---|---|---|---|---|
| | | 0 minutes | 15 Minutes | 30 Minutes | 45 minutes | 60 Minutes |
| 1 | hydrazine | 0 | 0.32 | 2.893 | 2.957 | — |
| 2 | hydrazide | 0.033 | 0.07 | 0.23 | 0.444 | 0.653 |
| 3 | dihydrazide | 0 | 0.055 | 0.148 | 0.172 | 0.172 |

This versatile methodology was therefore selected as an exemplary methodology for the conjugation and generation of various reducing moiety to the protein surface.

In accord with the main objective, the general description presented above and the selected conjugation method, exemplary bi-functional chemical moieties, having two or more amine or aldehydes groups, which upon conjugation potentially provide a reducing moiety, were studied. These include, for example, glutaraldehyde and its polymerization derivatives, adipic-dihydrazide and hydrazine.

As is detailed hereinbelow, various features regarding the reducing moiety, the preparation of enzymes having the reducing moieties attached to their surface and the activity of these enzymes prior and subsequently to each activation and modification steps have been studied.

Kinetic Studies of Silver Reduction by Hydrazine and Acylhydrazide:

Hydrazine is a known powerful reducer of silver, however, its reduction activity with silver is expected to result in an amorphous deposition of the metal, rapidly formed even at neutral pH. It was assumed that due to the reduced reduction aptitude thereof, acylhydrazide derivatives of hydrazine would exhibit milder, more controllable reaction rates that would lead to the desired crystalline silver deposits. As is detailed hereinbelow, kinetic studies regarding silver reduction by various chemical moieties that may act as reducing moieties upon conjugation to the enzyme were tested.

Kinetic measurements of the reduction in solution of silver nitrate by hydrazine, formic hydrazide and adipic dihydrazide were carried out by monitoring the turbidity generated by the formation of solid silver precipitant. Adipic dihydrazide appeared to be a promising reducing agent since it includes two functional groups that are separated by a four-carbon spacer and thus exhibits a reducing aptitude along with con- The kinetic parameters of the reduction of silver nitrate in each of these solutions are further presented in FIG. 1a.

As shown in FIG. 1a, the reduction rate of hydrazine was significantly higher than that of the hydrazides of formic and adipic acid. However, as can be seen in the HRTEM micrographs presented in FIGS. 1b-d, the metallic silver formed by reduction by hydrazine (FIG. 1b) was obtained as amorphous metal, whereby due to the milder and more linear rate of reduction exhibited by both formic hydrazide (FIG. 1c) and adipic-dihydrazide (FIG. 1d), highly ordered metallic silver crystals were obtained in their presence.

These results clearly demonstrate the highly controllable, hence more desired, reduction rate of the hydrazides as compared to that of hydrazine, which may thus lead to the formation of crystalline silver deposits. In addition, the milder and most controllable silver reduction exhibited by adipic-dihydrazide, combined with the abovementioned conjugation capabilities, indicated that this agent may serve as a suitable reducing agent for use in the context of the present invention.

Reduction Aptitude of Various Schiff-Bases of Glutaraldehyde

Aldehydes such as formaldehyde are effective silver reducers. Formaldehyde, in particular, is routinely employed under basic pH values for silver-stain detection of proteins separated by gel electrophoresis. Pre-treatment of denatured proteins embedded in polyacrylamide gels with 10% glutaraldehyde solution allowed for higher staining sensitivity, explained by the display of free aldehyde groups on protein surface. It was suggested [see, Dion and Pomenti, *Anal. Biochem.* 1983, 129, pp. 490-496], that these groups may serve as preferable nucleation sites for silver staining by the "developer" formaldehyde/ammoniacal silver solution.

A similar effect was observed for glycoproteins [see, Dubray and Bezard, *Anal. Biochem.* 1982, 325-329]. Thus, it was shown that the sensitivity of formaldehyde/ammoniacal silver staining of denatured proteins in polyacrylamide gels was substantially improved by the generation of aldehyde groups on these proteins by periodate oxidation.

In view of the findings above, and in order to gain insight into the question of suitable chemical moieties which would be appropriate for the abovementioned conjugation method, and thus for introducing reducing moieties to the protein surface, glutaraldehyde, a readily generated aldehyde moiety on protein surfaces, and three amine-glutaraldehyde Schiff-base derivatives, were tested for their silver nitrate reduction aptitude. The three amines used for forming the glutaraldehyde Schiff-bases were ammonia ($NH_3$), N,N-diethyl ethylenediamine and β-alanine (adding a negatively charged carboxyl group to the formed Schiff-base). The silver reduction reaction, expressed by precipitation of solid metallic silver, was followed spectroscopically by measuring the differences in the optical density at 425 nm.

Glutaraldehyde Schiff-bases were prepared by adding 1.6 ml of a 0.25 M solution of each amine in 0.05 M HEPES buffer, set to pH 7.5, to 0.2 ml of a 0.5 M solution of glutaraldehyde in water, and 8.2 ml of 0.05 M HEPES buffer, set to pH 7.5. Hence, the final concentration of glutaraldehyde was 5 mM, and the final concentration of the amine was 20 mM. The mixtures were incubated for 2 hours at room temperature.

Thereafter, 0.02 ml of a 0.5 M solution of silver nitrate were added to 10 ml of a 5 mM glutaraldehyde in water and to 10 ml of the abovementioned glutaraldehyde Schiff-bases solutions, and the resulting solutions were incubated for 2 hours at room temperature.

The turbidity generated by the solid silver precipitant after the incubation period was measured by the differences in the optical density of the tested solution before and after the incubation, at 435 nm.

The results of silver-reduction aptitude of glutaraldehyde and the series of glutaraldehyde-Schiff-base with ammonia, N,N-diethyl ethylenediamine and β-alanine are presented in Table 3 below.

TABLE 3

| | Tested Sample | $\Delta OD_{435}$ |
|---|---|---|
| 1 | Glutaraldehyde | 0.004 |
| 2 | Glutaraldehyde-β-alanine | 1.635 |
| 3 | Glutaraldehyde-N,N-diethyl ethylenediamine | 0.132 |
| 4 | Glutaraldehyde-NH3 | 0.294 |

The results clearly indicate that the imines (Schiff-bases) formed between the glutaraldehyde and the various amines were significantly more effective as reducing moieties for silver than glutaraldehyde, their parent free aldehyde. The degree of silver reduction by the glutaraldehyde-derived Schiff-base showed clear dependency on the specific amine employed, identifying β-alanine as superior to the other amines tested by 5.6 fold with respect to the glutaraldehyde-Schiff-base of ammonia and 12.4 fold with respect to the glutaraldehyde-Schiff-base of N,N-diethyl ethylenediamine.

Activation and Modification of Naturally Occurring Functional Groups of the Surface of the Enzymes:

In view of the above preliminary studies and results, and in order to accomplish the selected method of conjugation and generation of reducing moieties on the surface of proteins, according to the present invention, reactive aldehyde groups were generated or introduced onto the surface of the selected enzymes. To this end, naturally occurring functional moieties on the surface of the enzymes, such as the diol functional groups of glycan residues, and free amine groups of lysine residues and/or the N-terminal amino acid residue of the polypeptide chain, were readily converted to aldehydes, as is detailed hereinafter. The obtained aldehydes served as reactive groups for the following conjugation under mild and controllable conditions, of reducing moieties in the form of imines and/or hydrazides onto the surface of the enzymes.

In one embodiment of the methodology described above, diol groups of glycan residues were converted into aldehydes by oxidation thereof with periodate.

Oxidation with periodate was performed by mixing 5 ml of an enzyme solution, containing 5 mg glucose oxidase or peroxidase per 1 ml of 0.1 M HEPES buffer at pH 7.2, with 0.5 ml of a sodium periodate solution containing 19.4 mg $NaIO_4$ per 1 ml of highly purified water. The mixture was incubated for 20 minutes at 4° C. The activated enzyme was then purified by dialysis against water at 4° C. for 3 hours.

In another embodiment of the methodology described above, amine groups of lysine residues were converted into aldehydes by conjugating glutaraldehyde or polyglutaraldehyde (PGA) thereto. Reaction of free amine groups derived from lysine residues with glutaraldehyde or polymeric glutaraldehyde (PGA), was performed as described by Tor et al. [*Enz. Microb. Technol.* 1989, 11, pp. 306-312]. In brief, a mixture 25 mg of glucose oxidase or peroxidase in 5 ml solution of 0.076 M glutaraldehyde or PGA, and 0.05 M HEPES buffer at pH 8 was prepared and incubated overnight at 4° C. The resulting activated enzyme was then purified by dialysis against water at 4° C.

The activated enzymes, having lysine-glutaraldehyde/PGA residues or periodate-treated glycan residues on their surface, were then reacted with adipic-dihydrazide, as follows: 1.74 ml of an activated enzyme solution (starting with a solution of 5 mg per 1 ml of highly purified water) were mixed with an adipic-dihydrazide solution at a final concentration of 0.066 mM adipic-dihydrazide in highly purified water. The mixture was incubated for 3 hours at 4° C. The resulting modified enzyme was then purified by dialysis overnight against water at 4° C.

Scheme 3 below illustrates schematically the conjugation reaction described above, wherein P represents the enzyme residue to which a reactive aldehyde group is attached. Upon conjugation, a Schiff-base is formed between the aldehyde on the enzyme surface and one of the hydrazide groups of adipic-dihydrazide, while the second hydrazide functional group remains free, and thus may act as a reducing moiety.

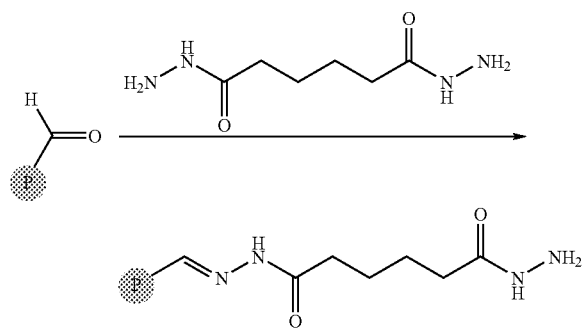

Scheme 3

Alternatively, the activated enzymes, having lysine-glutaraldehyde/PGA residues or periodate-oxidized glycan residues on their surface, were reacted with β-alanine, as follows: 2.6 ml of an activated enzyme solution (3 mg per 1 ml of highly purified water) were mixed with β-alanine solution at final concentration of 0.066 mM β-alanine in highly purified water at pH 7. The mixture was incubated for 3 hours at 4° C. The resulting modified enzyme was then purified by dialysis overnight against water at 4° C.

Scheme 4 below illustrates schematically the conjugation reaction described above, wherein P represents the enzyme residue to which a reactive aldehyde group is attached. Upon conjugation, a Schiff-base is formed between the aldehyde on the enzyme and the amine groups of β-alanine.

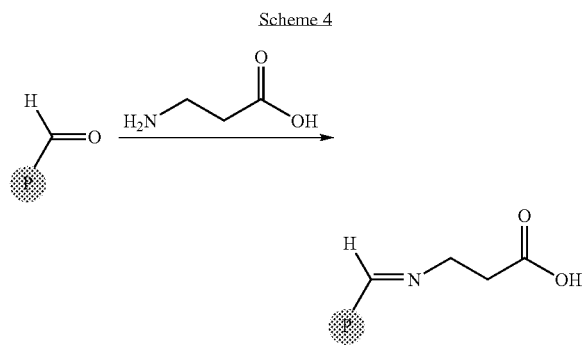

Scheme 4

In summary, two routes for preparing modified glucose oxidase and peroxidase, capable of effecting site-directed silver deposition on their surface, are described hereinbelow:

(i) providing an "activated enzyme" by oxidation of surface glycan residues with periodate, which results in the generation of reactive aldehyde groups on the surface of the enzyme, followed by conjugation to adipic-dihydrazide or β-alanine.

(ii) providing an "activated enzyme" by treating surface lysine residues with glutaraldehyde or PGA, which results in the introduction of reactive aldehyde groups on the surface of the enzyme, followed by conjugation to β-alanine.

Preparation of Silver-Metallized Enzymes:

Using the modified enzymes described above, the site-directed silver deposition on the enzymes surface was performed.

Thus, modified glucose oxidase or peroxidase (2.5 mg enzyme per 1 ml of highly purified water), having the above-mentioned reducing moieties attached thereto, were incubated overnight with a silver nitrate solution (10 mM $AgNO_3$) at room temperature. The resulting silver-coated enzymes were then purified by dialysis against water at 4° C.

The site-directed silver deposition process was analyzed by HRTEM, and an exemplary obtained micrograph is presented in FIG. 4. Specifically, FIG. 4 presents a HRTEM micrograph of a layer of silver atoms deposited on a silver-coated glucose oxidase, which was activated by treatment of the diol surface groups with periodate, followed by conjugation of the formed aldehyde groups to β-alanine so as to introduce the required reducing moiety onto the surface of the enzyme. The HRTEM micrograph, obtained without further staining of the sample, clearly show a patch of about 11 nm in diameter of metallic silver on the surface of the enzyme, exhibiting a well ordered crystalline morphology.

The two site-directed silver deposition routes were further analyzed kinetically by monitoring the rate of turbidity generation by the metallic silver particles formed on the surface of the enzymes.

The reduction reaction on the surface of the modified enzyme glucose oxidase (Gox) was measured by the differences in the optical density at 450 nm ($\Delta OD_{450}$) of the silver nitrate solution before and after the reduction reaction. The tested solutions were prepared by adding 0.02 ml of a 4 mM silver nitrate (final concentration of silver nitrate was 10 mM) to two sets of samples representing various stages of each of the enzyme modification routes described hereinabove, as is detailed hereinbelow and is further presented in FIGS. 2 and 3.

For the route utilizing periodate oxidation, the tested samples were:

1 ml of a 4.5 mg/ml solution of native glucose oxidase (denoted Gox+Ag);

1 ml of a 4.5 mg/ml solution of glucose oxidase treated with periodate (denoted Gox-$IO_4^-$+Ag);

1 ml of a 3.3 mg/ml solution of glucose oxidase treated with periodate and β-alanine (denoted Gox-$IO_4^-$-bala+Ag);

For the route utilizing glutaraldehyde/polyglutaraldehyde modification, the tested samples were:

1 ml of a 4.9 mg/ml solution of glucose oxidase treated with glutaraldehyde (denoted Gox-ga+Ag);

1 ml of a 4.5 mg/ml solution of glucose oxidase treated with polyglutaraldehyde (denoted Gox-pga+Ag);

1 ml of a 4.7 mg/ml solution of glucose oxidase treated with glutaraldehyde and β-alanine (denoted Gox-ga-bala+Ag); and 1 ml of a 3 mg/ml solution of glucose oxidase treated with polyglutaraldehyde and β-alanine (denoted Gox-pga-bala+Ag).

The results of the reduction reaction on the surface of the modified enzyme glucose oxidase, expressed in $\Delta OD_{398}$, are presented in FIG. 2, for glucose oxidase activated by the periodate oxidation route, followed by conjugation to β-alanine, and in FIG. 3, for glucose oxidase activated by conjugation of glutaraldehyde/polyglutaraldehyde to lysine residues, followed by conjugation to β-alanine.

As is shown in both FIGS. 2 and 3, native glucose oxidase displayed insignificant rate of silver reduction (plot denoted Gox+Ag).

As is further shown in FIG. 2, a low rate of silver reduction was observed with glucose oxidase activated with periodate (plot denoted Gox-$IO_4^-$+Ag). In contrast, a substantial increase in the rate of silver reduction was observed with glucose oxidase activated with periodate and conjugated to β-alanine (plot denoted Gox-$IO_4^-$-bala+Ag) as compared with the enzyme treated only with periodate.

As is further shown in FIG. 3, glucose oxidase activated with glutaraldehyde (plot denoted Gox-ga+Ag) also displayed low rate of silver reduction, as expected from the less reactive aldehyde groups introduced onto the surface of the enzyme. A higher rate of silver reduction was observed with glucose oxidase activated with polyglutaraldehyde (plot denoted Gox-pga+Ag in FIG. 3), possibly due to the larger number of aldehyde groups present on the surface of the enzyme, and their greater steric freedom. Glucose oxidase treated with glutaraldehyde, and further treated with β-alanine, displayed an improved rate of silver reduction (plot denoted Gox-ga-bala+Ag) as compared to its parent glutaraldehyde derivative.

Glucose oxidase treated with polyglutaraldehyde and conjugated to β-alanine displayed the highest rate of silver reduction as compared with all other samples presented herein (plot denoted Gox-pga-bala+Ag). These results clearly demonstrate the superior reduction potential of a Schiff-base moiety attached to the surface of a protein, particularly as compared with its parent aldehyde moiety.

Preparation of Doubly Silver-Metallized Enzymes:

Using the methodologies described above, doubly-coated enzymes were prepared as follows:

Silver-coated glucose oxidase was prepared by mixing modified glucose oxidase, treated with polyglutaraldehyde and conjugated to β-alanine, as described hereinabove with a 10 mM solution of silver nitrate, and incubating the mixture for 2 hours at room temperature. In parallel, a reducing solution was prepared by mixing polyglutaraldehyde (0.1 ml, 0.076M), β-alanine (0.6 ml, 0.25 M) and highly purified water (0.8 ml), and incubating the mixture for 2 hours at room temperature. Thereafter, the silver-coated glucose oxidase (1 ml) was mixed with the reducing solution (0.5 ml), and the mixture was incubated overnight at room temperature, to thereby obtain the doubly silver-metallized enzymes.

Enzymatic Activity and Dissolvability Assays of Silver-Coated Enzymes:

The effect of silver deposition on the enzymatic activity of the silver-coated enzymes obtained by the methodologies presented hereinabove was studied by measuring the specific activity of native glucose oxidase and peroxidase, and comparing it to the residual specific activity of the enzymes after each step of the process for obtaining the silver-coated enzymes.

The activity assays were performed as previously described by Blank-Koblenz et al. [*Biotechnol. Appl. Biochem.* 1988, 10, 32-41].

The effect of silver deposition on the dissolvability of the untreated and silver-coated enzymes was evaluated visually.

The following samples were used in these activity and dissolvability assays:

1. Untreated enzymes (peroxidase and glucose oxidase);
2. Periodate-treated enzymes;
3. Periodate and adipic-dihydrazide-treated enzymes;
4. Periodate and adipic-dihydrazide-treated enzymes upon deposition of silver;
5. Periodate and β-alanine-treated enzymes;
6. Periodate and β-alanine-treated enzymes upon deposition of silver;
7. Polyglutaraldehyde-treated enzymes;
8. Polyglutaraldehyde and β-alanine-treated enzymes;
9. Polyglutaraldehyde and β-alanine-treated enzymes upon deposition of silver; and
10. Polyglutaraldehyde and β-alanine-treated enzymes upon double silver deposition.

The obtained results are presented in Table 4 below.

The activity and dissolvability of the native (untreated) enzymes are presented in entry 1 of Table 4, and serve as a control standard for enzymatic activity and dissolvability to which the results obtained for the treated enzyme sample are compared.

Comparing the results obtained with glucose oxidase to those obtained with peroxidase generally indicate that both enzymes undergo the metallization process described above, while retaining a significant level of their activity and dissolvability. The results also highlight the greater overall sensitivity of glucose oxidase to each of the activation, modification and metallization steps applied, as compared with the relative durability of peroxidase.

Thus, the residual activity of glucose oxidase following treatment with periodate or polyglutaraldehyde was less than 50%, whereby the residual activity of proxidase following the same treatments was nearly 90% (see, entries 2 and 7 in Table 4). No effect on the dissolvability of both enzymes was recorded after these treatments.

The residual activity of glucose oxidase following treatment with periodate and conjugation to adipic-dihydrazide was 35%, whereby residual activity of proxidase following the same treatments was less than 90% (see, entry 3 in Table 4). No effect on the dissolvability of both enzymes was recorded after these treatments.

The residual activity of glucose oxidase following treatment with periodate, conjugation to adipic-dihydrazide and deposition of silver was less than 5%, whereby residual activity of proxidase following the same treatments was nearly 30% (see, entry 4 in Table 4). Following these treatments, glucose oxidase precipitated, whereby the solution of peroxidase following the same treatments became turbid.

The residual activity of glucose oxidase following treatment with periodate and conjugation to β-alanine was less than 35%, whereby residual activity of proxidase following the same treatments was nearly 90% (see, entry 5 in Table 4). No effect on the dissolvability of both enzymes was recorded after these treatments.

The residual activity of glucose oxidase following treatment with periodate, conjugation to β-alanine and deposition of silver was nearly 20%, whereby residual activity of proxidase following the same treatments was more than 40% (see, entry 6 in Table 4). Following these treatments, glucose oxidase precipitated, whereby the solution of peroxidase following the same treatments became turbid.

The residual activity of glucose oxidase following treatment with polyglutaraldehyde and conjugation to β-alanine was less than 30%, whereby residual activity of proxidase following the same treatments was less than 90% (see, entry

TABLE 4

| | | Peroxidase | | Glucose oxidase | |
|---|---|---|---|---|---|
| Enzyme Treatment | | % of Residual Specific activity | Dissolvability | % of Residual Specific activity | Dissolvability |
| 1 | Untreated | 100 | CLEAR | 100 | CLEAR |
| 2 | Periodate oxidation ($IO_4^-$) | 89 | CLEAR | 44 | CLEAR |
| 3 | $IO_4^-$ + Adipic dihydrazide (ADH) | 86 | CLEAR | 35 | CLEAR |
| 4 | $IO_4^-$ + ADH + $Ag^+$ | 29 | TURBID | 4 | PRECIPITATE |
| 5 | $IO_4^-$ + β-alanine | 88 | CLEAR | 33 | CLEAR |
| 6 | $IO_4^-$ + β-alanine + $Ag^+$ | 41 | TURBID | 19 | PRECIPITATE |
| 7 | Polyglutaraldehyde (PGA) | 88 | CLEAR | 49 | CLEAR |
| 8 | PGA-β-alanine | 87 | CLEAR | 27 | CLEAR |
| 9 | PGA-β-alanine + $Ag^+$ | 72 | TURBID | 20 | TURBID |
| 10 | PGA-β-alanine + $Ag^+$ x2 | 74 | TURBID | 19 | TURBID |

8 in Table 4). No effect on the dissolvability of both enzymes was recorded after these treatments.

The residual activity of glucose oxidase following treatment with polyglutaraldehyde, conjugation to β-alanine and silver deposition was 20%, whereby the residual activity of proxidase following the same treatments was more than 70% (see, entry 9 in Table 4). Following these treatments, the solution of both glucose oxidase and precipitated became turbid, but both enzymes remained dissolvable. The same results were recorded when the thickened silver metallization procedure (double silver deposition) was applied for both enzymes (see, entry 10 in Table 4).

These results clearly indicate that using the methodologies for depositing silver on the surface of enzymes, described hereinabove, silver-coated peroxidase which retains almost 75% of its native activity, and substantially maintains its dissolvability, and silver-coated glucose oxidase which retains about 20% of its native activity, and substantially maintains its dissolvability are obtained. These results further indicate that activation of both enzymes with polyglutaraldehyde followed by conjugation of β-alanine provided the most efficient modified enzymes in terms of the dissolvability and retained activity of the silver-coated enzymes obtained therefrom.

Antibacterial and Fungistatic Activity of Silver-Metallized Glucose Oxidase:

The anti-bacterial and anti-fungal activity of silver-coated glucose oxidase was assayed as follows:

Targeted microorganism samples were grown in various Difco® culture media under shaking overnight at 30° C., using the following growth media: *T. rubrum* was grown under shaking in Sabouraud glucose agar (SDA) or broth (SDB) medium for two days at 30° C.; *S. aureus* was grown in tryptic soy agar (TSA) or broth (TSB); and *E. coli* and *B. megaterium* was grown under shaking in Luria-Bertani (LB) medium with glucose or LB with agar (15%) overnight at 30° C. A 20 μl sample of each of the targeted organisms were used to inoculate 100 μl wells of ELISA plates furnished with nutrient agar, and were allowed to grow for 2 hours prior to introduction to silver-metallized glucose oxidase.

The two samples of silver-coated glucose oxidase which displayed the highest residual activity and dissolvability, as presented in Table 4 above, were tested for their antibacterial activity. These samples included a silver-coated glucose oxidase obtained by activating the enzyme with polyglutaraldehyde, followed by conjugation to β-alanine, and further followed by silver deposition, as described in detail hereinabove and a doubly-coated glucose oxidase obtained by activating the silver-coated enzyme with polyglutaraldehyde, followed by conjugation to β-alanine, and further followed by deposition of an additional silver coating thereon. Fifty microliters of a silver-coated enzyme solution (5 mg/ml in water) of each of the abovementioned samples were added to the ELISA plate wells containing the targeted organisms. Water or null was added to the controls wells.

The bacterial samples were tested for the antibacterial and fungistatic activity of the silver-coated enzyme after 1 and 5 days, by monitoring colonies growth under a stereomicroscope.

The results indicated that the presence of silver-coated glucose oxidase in wells containing bacterial cultures caused inhibition of cell growth.

Images of the ELIZA plates in which the microorganism samples were grown in the presence and absence (control) of silver-coated glucose oxidase are presented in FIG. 5*a* (following 1 day) and FIG. 5*b* (following 5 days).

As can be seen in FIGS. 5*a* and 5*b*, the growth of the three bacterial strains tested was substantially inhibited in the presence of both samples of silver-coated glucose oxidase, while the doubly-metallized enzyme was found to more effective than the singly-metallized enzyme.

Preparation and Use of Glucose Biosensors Using Silver-Metallized Glucose Oxidase:

Micro-electrodes were prepared by depositing various solutions of glucose oxidase at various stages of the treatment on the path to the doubly silver-metallized glucose oxidase, as is detailed below, onto screen-printed electrodes. Glucose oxidase solutions (2 μl), having a protein concentration of 3 mg/ml in double distilled water, were deposited onto a carbon-ink disposable working screen-printed electrode (Gwent, UK) and the electrode was thereafter allowed to dry at room temperature. The electrodes were then covered with nation (0.05%), a composition that is able to conduct solvated hydrogen ions but not electrons, and were thereafter allowed to dry.

A β-Glucose solution (200 mM) was prepared and was mutarotated over night before use. The various screen-printed electrodes, having glucose oxidase deposited thereon were dipped in an electrolyte solution containing phosphate buffer solution (0.1 M, pH 7), KCl (0.1 M) and ferrocene monocarboxylic acid (1 mM) as a mediator, at room temperature. Each electrochemical cell further included an Ag/AgCl reference electrode and a carbon-ink counter electrode.

Glucose determination assays were conducted by adding the glucose solution to the electrochemical measuring cell at constant time intervals. The resulting current was automatically recorded using BAS potentiostat (Bio-Analytical Systems, US) set to a scan rate of 50 mV per second.

In electrodes having silver-coated enzyme deposit, throughout the first potential scan, some of the silver in the thin metallic coating layer was oxidized into $Ag+$, which immediately reacted with Fc, returning to its metallic state and increasing the near-surface concentration of $Fc+$ levels, which were in turn ready to react again with the reduced enzyme.

FIG. 7 presents comparative plots of cyclic voltammograms of electro-catalytic currents (in microamperes) plotted versus electric potential (in millivolts) as recorded for five samples of glucose-oxidase at various stages of preparation of the silver-metallized enzyme, marked as follows:

(a) untreated glucose oxidase;

(b) polyglutaraldehyde-treated glucose oxidase;

(c) polyglutaraldehyde and β-alanine-treated glucose oxidase;

(d) polyglutaraldehyde and β-alanine-treated glucose oxidase coated with silver; and (e) polyglutaraldehyde and β-alanine-treated glucose oxidase doubly coated with silver.

FIG. 8 presents comparative plots of electro-catalytic peak currents plotted versus glucose concentration as recorded for three samples of glucose-oxidase at various stages of preparation of the silver-metallized enzyme, marked as follows:

untreated glucose oxidase in blue diamonds (corresponding to sample "a" above);

Silver-metallized glucose oxidase in magenta rectangles (corresponding to sample "d" above); and Doubly silver-metallized glucose oxidase in green triangles (corresponding to sample "e" above).

As can be seen in FIGS. 7 and 8, the highest electro-catalytic peak current was recorded, and hence a superior performance, was obtained with the electrode having the doubly-metallized glucose-oxidase enzyme deposited thereon, demonstrating the beneficial use of silver-coated enzymes, and especially the doubly-coated enzymes of the present invention, as glucose biosensors.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A composition-of-matter comprising a protein having a solvent-accessible surface and further having a biological activity and a metallic silver coating deposited over said surface and forming a silver-coated protein retaining said biological activity, wherein said protein has at least one oxidized reducing moiety attached to at least a portion of said surface, said reducing moiety being selected from the group consisting of hydrazine, hydrazide and imine, said oxidized reducing moiety being obtained upon reducing silver ions to form said metallic silver coating, said silver coating is in a form of a continuous metallic silver layer covering 0.1% to 60% of said surface, and wherein said protein is a hydrogen peroxide producing enzyme and said biological activity is a catalytic reaction activity.

2. The composition-of-matter of claim 1, wherein said silver-coated protein is dissolvable or suspendable in an aqueous medium.

3. A pharmaceutical composition for the treatment of a bacterial and/or fungal infection, comprising, as an active ingredient, the composition-of-matter of claim 1 and a pharmaceutically acceptable carrier.

4. The pharmaceutical composition of claim 3, packaged in a packaging material and identified in print, in or on said packaging material, for treatment of said infection.

5. The composition-of-matter of claim 1, wherein said reducing moiety is imine.

6. The composition-of-matter of claim 5, wherein said protein having an oxidized imine attached to at least a portion of a surface thereof is obtained upon conjugating a polyaldehyde to said protein's surface.

7. The composition-of-matter of claim 1, wherein said reducing moiety is selected from the group consisting of hydrazide and imine.

8. The composition-of-matter of claim 7, wherein said oxidized reducing moiety is attached to said surface via an aldehyde group generated on said surface.

9. The composition-of-matter of claim 8, wherein said reducing moiety is formed upon conjugating a chemical moiety to said aldehyde group.

10. The composition-of-matter of claim 9, wherein said chemical moiety is selected from the group consisting of β-alanine and adipic-dihydrazide.

11. A process of preparing the composition-of-matter of claim 1, the process comprising:
providing a first aqueous solution containing silver ions;
providing a protein having a first reactive group on a surface thereof;
conjugating to said first reactive group a first chemical moiety selected such that upon said conjugating a protein having said reducing moiety attached to said surface is obtained, said reducing moiety being selected from the group consisting of hydrazine, hydrazide and imine; and
contacting said protein having said reducing moiety attached to said surface with said first aqueous solution, to thereby form said silver-coated protein, thereby obtaining the composition-of-matter.

12. The process of claim 11, wherein a substrate of said hydrogen peroxide producing enzyme is a sugar.

13. The process of claim 12, wherein said sugar is glucose.

14. The process of claim 13, wherein said enzyme is glucose oxidase.

15. A method of treating a bacterial and/or fungal infection, the method comprising administering to a subject in need thereof a therapeutically effective amount of a pharmaceutical composition comprising the composition-of-matter of claim 1.

16. The method of claim 15, wherein a substrate of said hydrogen peroxide producing enzyme is a sugar.

17. The method of claim 16, wherein said sugar is glucose.

18. The method of claim 17, wherein said enzyme is glucose oxidase.

* * * * *